(12) United States Patent
Yamate

(10) Patent No.: US 10,947,393 B2
(45) Date of Patent: Mar. 16, 2021

(54) COATING AGENT

(71) Applicant: NIPPON SODA CO., LTD., Tokyo (JP)

(72) Inventor: Taiki Yamate, Ichihara (JP)

(73) Assignee: NIPPON SODA CO., LTD., Tokyo (JP)

( * ) Notice: Subject to any disclaimer, the term of this patent is extended or adjusted under 35 U.S.C. 154(b) by 165 days.

(21) Appl. No.: 14/759,969

(22) PCT Filed: Nov. 27, 2013

(86) PCT No.: PCT/JP2013/006973
§ 371 (c)(1),
(2) Date: Jul. 9, 2015

(87) PCT Pub. No.: WO2014/115210
PCT Pub. Date: Jul. 31, 2014

(65) Prior Publication Data
US 2015/0353738 A1  Dec. 10, 2015

(30) Foreign Application Priority Data
Jan. 28, 2013 (JP) .............................. JP2013-013092

(51) Int. Cl.
| | | |
|---|---|---|
| C09D 4/00 | (2006.01) | |
| C07C 69/54 | (2006.01) | |
| C07C 69/007 | (2006.01) | |
| C07F 7/08 | (2006.01) | |
| C08J 7/04 | (2020.01) | |

(52) U.S. Cl.
CPC .............. *C09D 4/00* (2013.01); *C07C 69/007* (2013.01); *C07C 69/54* (2013.01); *C07F 7/081* (2013.01); *C08J 7/042* (2013.01); *C08J 7/0427* (2020.01); *C08J 2300/00* (2013.01); *C08J 2433/08* (2013.01); *C08J 2433/14* (2013.01); *C08J 2435/02* (2013.01); *C08J 2443/04* (2013.01); *Y10T 428/31663* (2015.04); *Y10T 428/31699* (2015.04); *Y10T 428/31935* (2015.04)

(58) Field of Classification Search
None
See application file for complete search history.

(56) References Cited

U.S. PATENT DOCUMENTS

| | | | | |
|---|---|---|---|---|
| 4,742,136 A | | 5/1988 | Uchida | |
| 4,752,629 A | * | 6/1988 | Proudlock | C09D 5/1668 523/122 |
| 4,960,465 A | * | 10/1990 | Arfaei | C04B 24/2647 106/724 |
| 5,393,823 A | * | 2/1995 | Konno | C09D 143/04 524/507 |
| 5,902,851 A | * | 5/1999 | Yamaki | C09D 4/06 524/506 |
| 6,197,913 B1 | | 3/2001 | Zhong | |
| 2002/0012872 A1 | * | 1/2002 | Kobayashi | G03F 7/0045 430/270.1 |
| 2003/0225184 A1 | | 12/2003 | Aubart et al. | |
| 2004/0138332 A1 | | 7/2004 | Aubart et al. | |
| 2004/0210023 A1 | * | 10/2004 | Salamone | C07F 7/0818 528/43 |
| 2006/0134546 A1 | | 6/2006 | Huang et al. | |
| 2010/0048802 A1 | * | 2/2010 | Hunt | C08F 32/06 524/548 |
| 2010/0197876 A1 | | 8/2010 | Lyu et al. | |
| 2011/0003957 A1 | | 1/2011 | Arishima et al. | |
| 2011/0280789 A1 | * | 11/2011 | Suzuki | H01M 4/133 423/445 R |

FOREIGN PATENT DOCUMENTS

| | | |
|---|---|---|
| CN | 1582289 A | 2/2005 |
| CN | 101627063 A | 1/2010 |
| EP | 0 204 444 A1 | 12/1986 |

(Continued)

OTHER PUBLICATIONS

English machine translation WO2009139476(2009).*

(Continued)

*Primary Examiner* — Kenneth J Stachel
(74) *Attorney, Agent, or Firm* — Oliff PLC

(57) ABSTRACT

It is an object to provide a coating agent that can form a layer having excellent adhesiveness to a plastic substrate and having transparency and a high refractive index. The coating agent of the present invention comprises a compound represented by formula (I) [wherein A represents a phenyl group or a naphthyl group optionally having an electron-donating group as a substituent; Z represents a carbon atom or a silicon atom, $R^2$ represents a hydrogen atom, a hydroxyl group, a linear or branched alkyl group, a linear or branched alkoxy group, a cyclic alkyl group, or a cyclic alkoxy group, X represents a single bond; an alkylene group optionally comprising an oxygen atom, a sulfur atom, a selenium atom, —NR—, a divalent aliphatic ring group, an arylene group, an amide structure or a urethane structure; a divalent aliphatic ring group; or an arylene group, Y represents a polymerizable functional group, n represents an integer of 2 or 3, m represents an integer of 1 or 2, l represents an integer of 0 or 1, and n+m+l=4; and when n represents an integer of 2 or 3, A is the same or different].

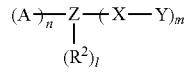

20 Claims, No Drawings

(56) References Cited

FOREIGN PATENT DOCUMENTS

| | | | |
|---|---|---|---|
| JP | S61-261374 A | | 11/1986 |
| JP | S63-145287 A | | 6/1988 |
| JP | S63-145310 A | | 6/1988 |
| JP | S63-286472 A | | 11/1988 |
| JP | H06-19147 A | | 1/1994 |
| JP | 09034113 A | * | 2/1997 |
| JP | 2001-131288 A | | 5/2001 |
| JP | 2002-309018 A | | 10/2002 |
| JP | 2003-080624 A | | 3/2003 |
| JP | 2004-035881 A | | 2/2004 |
| JP | 2004-346317 A | | 12/2004 |
| JP | 2005126622 A | * | 5/2005 |
| JP | 2011-85767 A | | 4/2011 |
| JP | 2011-201087 A | | 10/2011 |
| JP | 2012153825 A | * | 8/2012 |
| JP | 2013-091779 A | | 5/2013 |
| WO | 03/040152 A1 | | 5/2003 |
| WO | 2008/112452 A2 | | 9/2008 |
| WO | 2009/139476 A1 | | 11/2009 |
| WO | 2012/133586 A1 | | 10/2012 |

OTHER PUBLICATIONS

Englishmachinetranslation WO2012133586 (2012).*
English machine translation of JP09-034113.*
English machine translation JP2005-126622.*
English machine translation for JP 2012153835 (2012).*
English machine translation for JP63145287 (1988).*
Eng Translation Uchida Synthesis & Characteristics of Phenylsilyl Monomers (1987).*
Reactions of Surface Isocyanate Groups with Selected Compounds M L Unland Ji of Physical Chemistry vol. 79 No. 6 pp. 610-615 (1975).*
CAS Registry No. 32356-81-3.*
Oct. 1, 2014 Office Action issued in Taiwanese Application No. 102143579.
Jan. 7, 2014 International Search Report issued in International Application No. PCT/JP2013/006973.
Jul. 28, 2015 International Preliminary Report on Patentability issued in International Application No. PCT/JP2013/006973.
Sep. 5, 2016 Extended Search Report issued in European Patent Application No. 13872476.0.

* cited by examiner

COATING AGENT

TECHNICAL FIELD

The present invention relates to a novel coating agent, particularly a coating agent having excellent adhesiveness to a plastic substrate.

This application claims priority to Japanese Patent Application No. 2013-013092 filed on Jan. 28, 2013, the content of which is incorporated herein.

BACKGROUND ART

A compound having an aryl group is known as a monomer that provides a polymer having transparency and a high refractive index (optical material). For example, in Patent Documents 1 and 2, it is disclosed that a compound having a triphenylsilyl group can be used as an optical material such as a lens or a prism. In addition, in Patent Document 3, it is disclosed that a compound having four phenyl groups can be used for an optical element.

However, it is not known that coating agents containing these compounds have excellent adhesiveness to a plastic substrate.

PRIOR ART DOCUMENTS

Patent Documents

Patent Document 1: Japanese unexamined Patent Application Publication No. 63-145310
Patent Document 2: Japanese unexamined Patent Application Publication No. 63-145287
Patent Document 3: WO2009/139476

SUMMARY OF THE INVENTION

Object to be Solved by the Invention

It is an object to provide a coating agent that can form a layer having excellent adhesiveness to a plastic substrate and having transparency and a high refractive index.

Means to Solve the Object

As a result of diligent study for the solution of the above object, it has been found that a compound represented by formula (I) can provide a coating agent that forms a layer having excellent adhesiveness to a plastic substrate, leading to the completion of the present invention.

Specifically, the present invention relates to (1) A coating agent comprising a compound represented by formula (I):

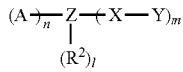

[wherein
A represents

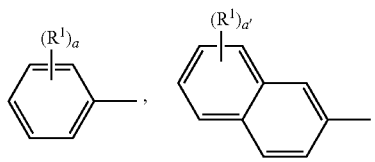

(wherein $R^1$ represents an electron-donating group, a represents an integer of 0 to 5, and a' represents an integer of 0 to 7),
Z represents a carbon atom or a silicon atom,
$R^2$ represents a hydrogen atom, a hydroxyl group, a linear or branched C1 to C6 alkyl group, a linear or branched C1 to C6 alkoxy group, a C3 to C6 cyclic alkyl group, or a C3 to C6 cyclic alkoxy group,
X represents a single bond;
a C1 to C20 alkylene group optionally comprising an oxygen atom, a sulfur atom, a selenium atom, —NR— (wherein R represents a hydrogen atom or a C1 to C6 alkyl group), a C3 to C6 divalent aliphatic ring group, a C6 to C10 arylene group, an amide structure or a urethane structure;
a C3 to C10 divalent aliphatic ring group;
or a C6 to C10 arylene group,
Y represents a polymerizable functional group,
n represents an integer of 2 or 3,
m represents an integer of 1 or 2,
l represents an integer of 0 or 1, and n+m+l=4; and
when n represents an integer of 2 or 3, A is the same or different].

(2) A coating agent comprising a compound represented by formula (I):

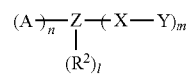

[wherein
A represents

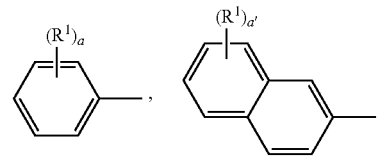

(wherein $R^1$ represents an electron-donating group, a represents an integer of 0 to 5, and a' represents an integer of 0 to 7),
Z represents a carbon atom or a silicon atom,
$R^2$ represents a hydrogen atom, a hydroxyl group, a linear or branched C1 to C6 alkyl group, a linear or branched C1 to C6 alkoxy group, a C3 to C6 cyclic alkyl group, or a C3 to C6 cyclic alkoxy group,
X represents a single bond;
a C1 to C20 alkylene group optionally comprising an oxygen atom, a sulfur atom, a selenium atom, —NR— (wherein R represents a hydrogen atom or a C1 to C6 alkyl group), a C3 to C6 divalent aliphatic ring group, a C6 to C10 arylene group, an amide structure or a urethane structure;
a C3 to C10 divalent aliphatic ring group;
or a C6 to C10 arylene group,
Y represents a polymerizable functional group,
n represents an integer of 2 or 3,
m represents 1,
l represents an integer of 0 or 1, and n+m+l=4; and
when n represents an integer of 2 or 3, A is the same or different].

(3) A coating agent comprising a compound represented by formula (I):

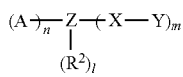

[wherein
A represents

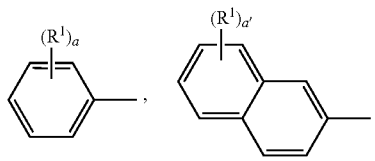

(wherein $R^1$ represents an electron-donating group, a represents an integer of 0 to 5, and a' represents an integer of 0 to 7), Z represents a carbon atom or a silicon atom, $R^2$ represents a hydrogen atom, a hydroxyl group, a linear or branched C1 to C6 alkyl group, a linear or branched C1 to C6 alkoxy group, a C3 to C6 cyclic alkyl group, or a C3 to C6 cyclic alkoxy group, X represents a single bond;
a C1 to C20 alkylene group optionally comprising an oxygen atom, a sulfur atom, a selenium atom, —NR— (wherein R represents a hydrogen atom or a C1 to C6 alkyl group), a C3 to C6 divalent aliphatic ring group, a C6 to C10 arylene group, an amide structure or a urethane structure; a C3 to 010 divalent aliphatic ring group;
or a C6 to C10 arylene group, Y represents a polymerizable functional group,
n represents 3,
m represents 1, and
l represents 0; and
A is the same or different].

(4) The coating agent according to any one of the above (1) to (3), wherein the coating agent comprising the compound represented by formula (I) further comprises a metal compound.

(5) The coating agent according to the above (4), wherein the metal compound is zirconia.

(6) The coating agent according to any one of the above (1) to (5), wherein the coating agent comprising the compound represented by formula (I) further comprises a condensate of an organosilane compound represented by formula (II):

$$R^4Si(R^3)_3 \quad (II)$$

(wherein $R^4$ represents a C2 to C8 alkenyl group, a C6 to C10 aryl group, or a C1 to C30 alkyl group optionally substituted by an epoxy group, a glycidyloxy group, or a (meth)acryloxy group, and $R^3$ represents a hydroxyl group or a hydrolyzable group).

(7) A compact, wherein the compact is directly provided with a layer obtained by coating a substrate with the coating agent according to any one of the above (1) to (6) and curing the coating agent.

(8) The compact according to the above (7), wherein the substrate is a plastic substrate.

(9) A compact, wherein a laminated film having functionality is further provided on the compact according to the above (7) or (8).

(10) The compact according to the above (9), wherein the laminated film having functionality is an indium tin oxide film.

Effect of the Invention

According to the present invention, it is possible to provide a coating agent that forms a high refractive index layer having excellent adhesiveness to a plastic substrate, particularly a cycloolefin polymer substrate. In addition, when the coating agent comprises a condensate of an organosilane compound, it can be utilized as an organic-inorganic composite film or a composition for forming the same. In addition, the layer formed by the coating agent of the present invention has excellent adhesiveness, and this layer can be used as an adhesive layer or an intermediate layer. A functional film with which a plastic substrate could not be conventionally directly coated can be laminated via the film of the present invention.

MODE OF CARRYING OUT THE INVENTION

1 Coating Agent
(Formula (I) Compound)

The coating agent of the present invention comprises a compound represented by the following formula (I). Only one compound represented by formula (I) or a mixture of two or more compounds represented by formula (I) can be used.

Formula (I)

wherein A represents

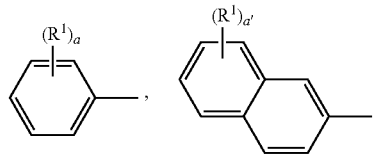

($R^1$ represents an electron-donating group, a represents an integer of 0 to 5, and a' represents an integer of 0 to 7), Z represents a carbon atom or a silicon atom, $R^2$ represents a hydrogen atom, a hydroxyl group, a linear or branched C1 to C6 alkyl group, a linear or branched C1 to C6 alkoxy group, a C3 to C6 cyclic alkyl group, or a C3 to C6 cyclic alkoxy group, X represents a single bond;
a C1 to C20 alkylene group optionally comprising an oxygen atom, a sulfur atom, a selenium atom, —NR— (wherein R represents a hydrogen atom or a C1 to C6 alkyl group), a C3 to C6 divalent aliphatic ring group, a C6 to C10 arylene group, an amide structure or a urethane structure; a C3 to C10 divalent aliphatic ring group;
or a C6 to C10 arylene group, Y represents a polymerizable functional group,
n represents an integer of 2 or 3,
m represents an integer of 1 or 2,
l represents an integer of 0 or 1, and n+m+l=4; and
when n represents an integer of 2 or 3, A is the same or different.

Examples of the electron-donating group of $R^1$ include a hydroxyl group, a C1 to C6 alkyl group, a C1 to C6 alkoxy group, a C1 to C6 alkylthio group, a C6 to C10 aryl group, and a C6 to C10 aryloxy group.

Specific illustrations of the electron-donating group of $R^1$ are as follows.

Examples of the "C1 to C6 alkyl group" include a methyl group, an ethyl group, a n-propyl group, an i-propyl group, a n-butyl group, a s-butyl group, an i-butyl group, a t-butyl group, a n-pentyl group, and a n-hexyl group.

Examples of the "C1 to C6 alkoxy group" include a methoxy group, an ethoxy group, a n-propoxy group, an i-propoxy group, a n-butoxy group, a s-butoxy group, an i-butoxy group, a t-butoxy group, a n-pentoxy group, and a n-hexoxy group.

Examples of the "C1 to C6 alkylthio group" include a methylthio group, an ethylthio group, a n-propylthio group, an i-propylthio group, a n-butylthio group, a s-butylthio group, an i-butylthio group, a t-butylthio group, a n-pentylthio group, and a n-hexylthio group.

Examples of the "C6 to C10 aryl group" include a phenyl group and a naphthyl group.

Examples of the "C6 to C10 aryloxy group" include a phenoxy group and a naphthoxy group.

Specific illustrations of the substituent of X are as follows.

The "C1 to C20 alkylene group" is a divalent carbon chain. Examples thereof include a methylene chain, a dimethylene chain, a trimethylene chain, a methyldimethylene chain, a tetramethylene chain, a 1,2-dimethyldimethylene chain, a pentamethylene chain, a 1-methyltetramethylene chain, a 2-methyltetramethylene chain, a hexamethylene chain, an octamethylene chain, a decamethylene chain, and an icosamethylene group.

Examples of the "C1 to C6 alkyl group" of R in —NR— include a methyl group, an ethyl group, a n-propyl group, an i-propyl group, a n-butyl group, a s-butyl group, an i-butyl group, a t-butyl group, a n-pentyl group, and a n-hexyl group.

Examples of the "C3 to C6 divalent aliphatic ring group" include a 1,1-cyclopropylene group, a 1,2-cyclopropylene group, a 1,2-cyclobutylene group, a 1,3-cyclobutylene group, a 1,2-cyclohexylene group, and a 1,4-cyclohexylene group.

Examples of the "C6 to C10 arylene group" include a 1,2-phenylene group, a 1,4-phenylene group, a 1,2-naphthylene group, and a 1,5-naphthylene group.

For the oxygen atom, the sulfur atom, and the selenium atom, for example, the oxygen atom encompasses —O— and —CO—.

Specific examples of X that is "a C1 to C20 alkylene group optionally comprising an oxygen atom, a sulfur atom, a selenium atom, —NR— (wherein R represents a hydrogen atom or a C1 to C6 alkyl group), a C3 to C6 divalent aliphatic ring group, a C6 to C10 arylene group, an amide structure or a urethane structure" include the following:

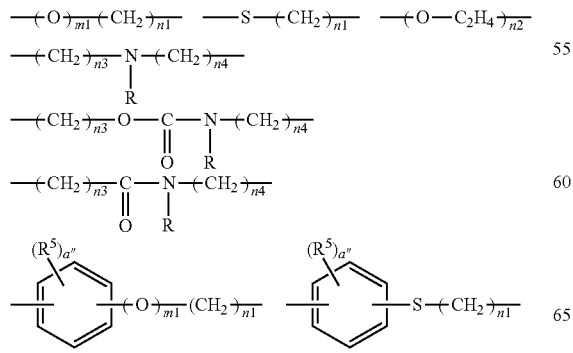

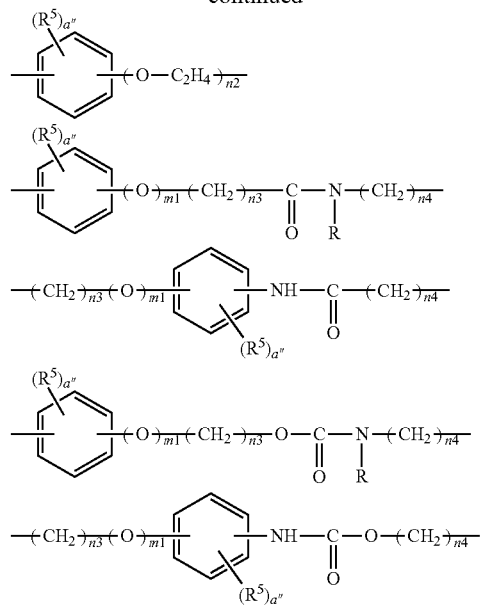

Among the above structures, structures represented by

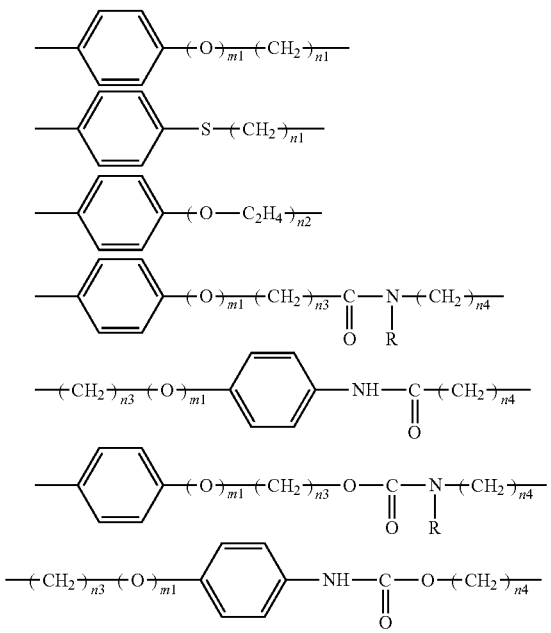

are preferred.

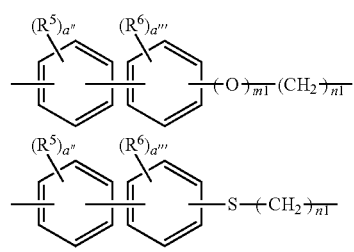

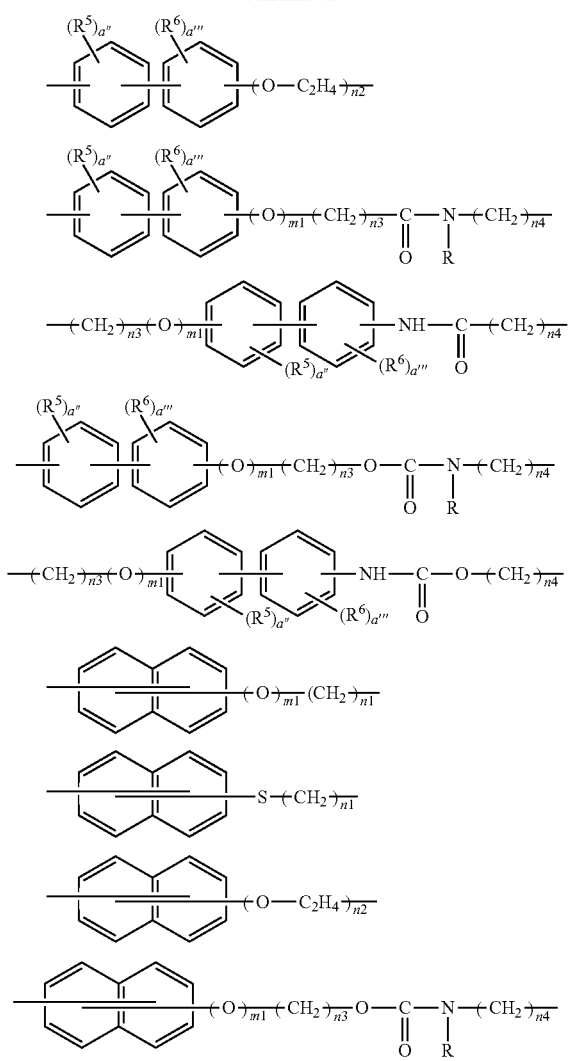

Among the above structures, structures represented by

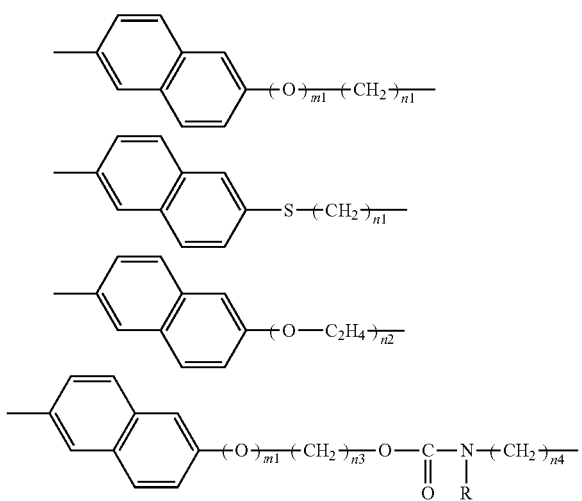

are preferred.

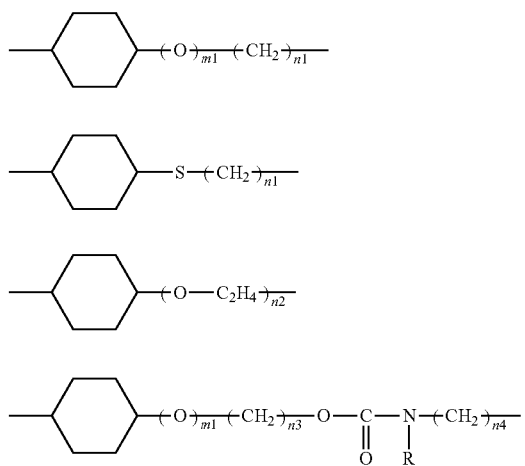

Here, $R^5$ and $R^6$ each represent an electron-donating group. Examples thereof include a hydroxyl group, a C1 to C6 alkyl group, a C1 to C6 alkoxy group, a C1 to C6 alkylthio group, a C6 to C10 aryl group, and a C6 to C10 aryloxy group.

Specific illustrations of the electron-donating groups of $R^5$ and $R^6$ are as follows.

Examples of the "C1 to C6 alkyl group" include a methyl group, an ethyl group, a n-propyl group, an i-propyl group, a n-butyl group, a s-butyl group, an i-butyl group, a t-butyl group, a n-pentyl group, and a n-hexyl group.

Examples of the "C1 to C6 alkoxy group" include a methoxy group, an ethoxy group, a n-propoxy group, an i-propoxy group, a n-butoxy group, a s-butoxy group, an i-butoxy group, a t-butoxy group, a n-pentoxy group, and a n-hexoxy group.

Examples of the "C1 to C6 alkylthio group" include a methylthio group, an ethylthio group, a n-propylthio group, an i-propylthio group, a n-butylthio group, a s-butylthio group, an i-butylthio group, a t-butylthio group, a n-pentylthio group, and a n-hexylthio group.

Examples of the "C6 to C10 aryl group" include a phenyl group and a naphthyl group.

Examples of the "C6 to C10 aryloxy group" include a phenoxy group and a naphthoxy group.

In addition, a" and a''' each independently represent an integer of 0 to 4, preferably 0 or 1, n1 represents an integer of 1 to 20, preferably an integer of 1 to 10, and more preferably an integer of 1 to 5.

n2 represents an integer of 1 to 10, preferably an integer of 1 to 5, and more preferably an integer of 1 to 2.

n3 and n4 each independently represent an integer of 1 to 10, preferably an integer of 1 to 5.

m1 represents an integer of 0 or 1.

Examples of the polymerizable functional group of Y include $-O-CO-(O)_{m2}-CR=CH_2$ (wherein m2 represents 0 or 1, and R represents a hydrogen atom or a methyl group), $-CH=CH_2$, an allyloxy group, an allyloxycarbonyloxy group, an epoxy group, or a functional group used to form a polyester, polyurethane, a polyisocyanate or a polycarbonate, such as

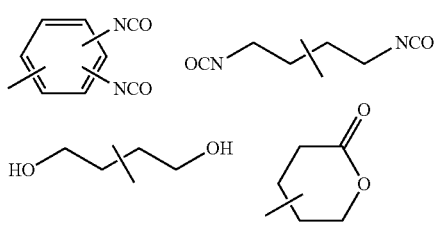
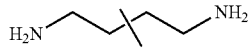
Specifically, as the compound represented by formula (I) according to the present invention, the following are illustrated.
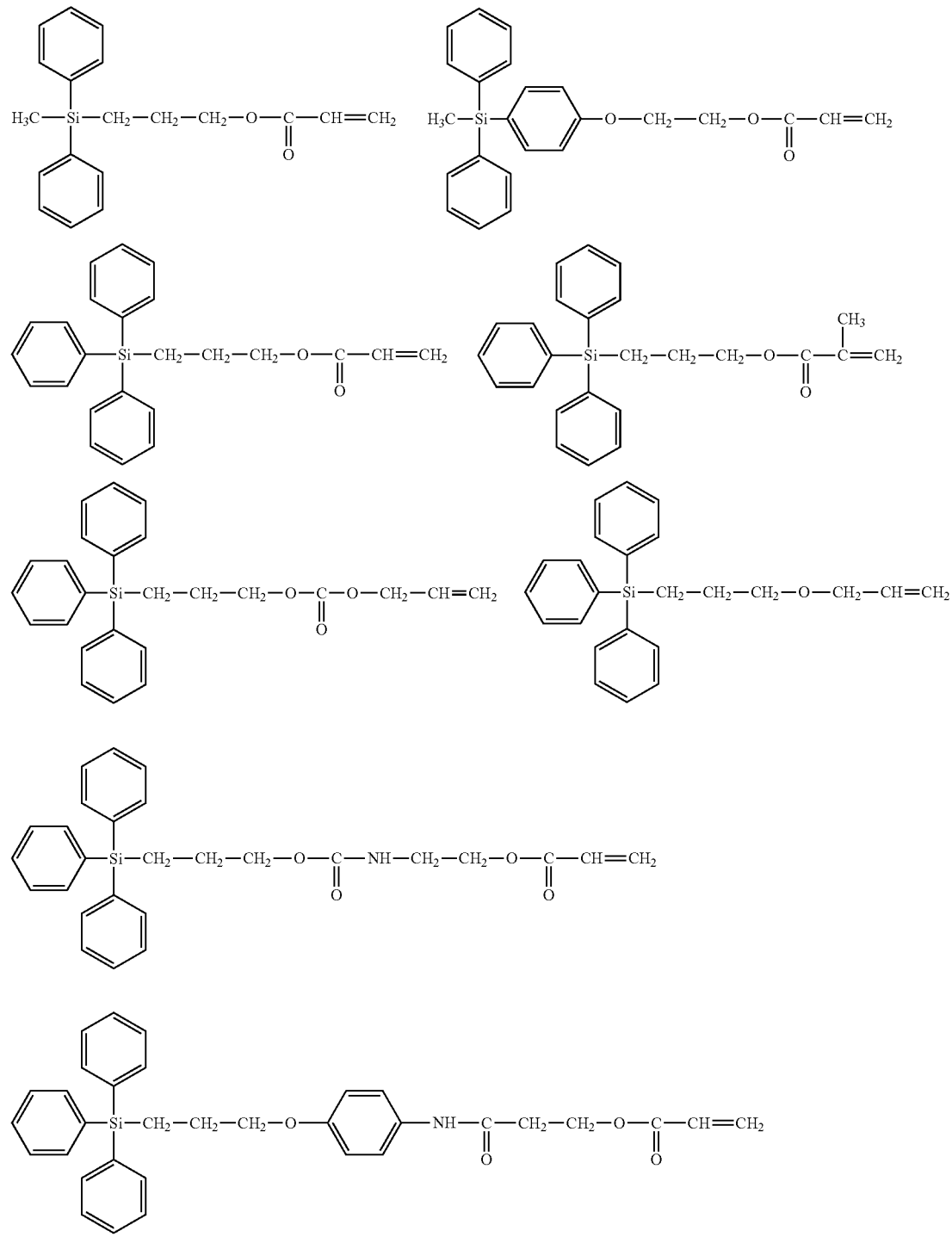

-continued
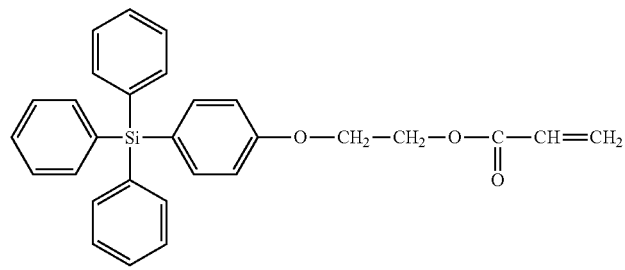
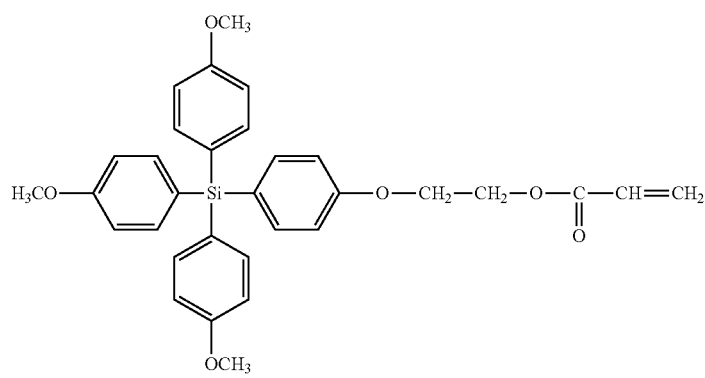
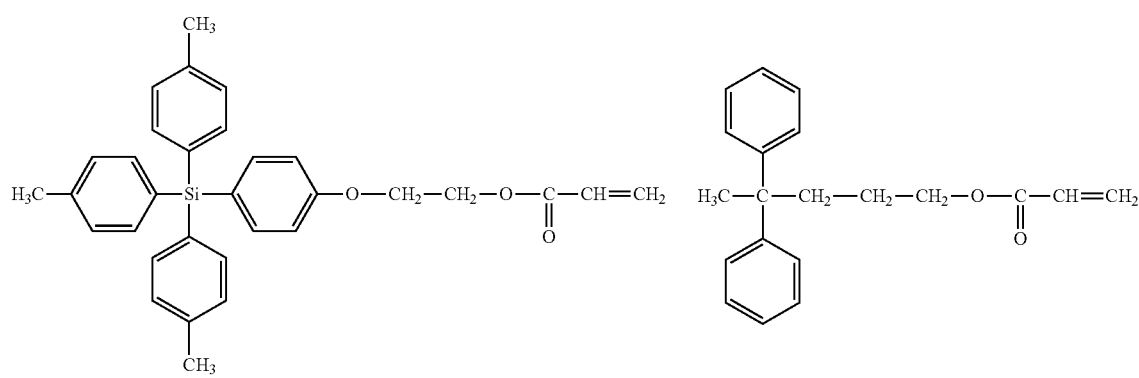
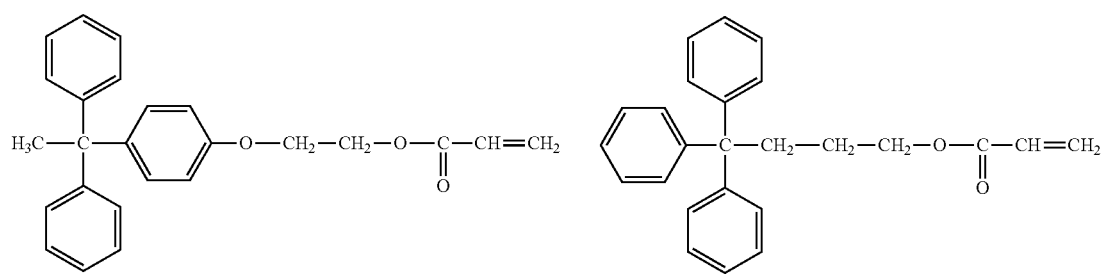
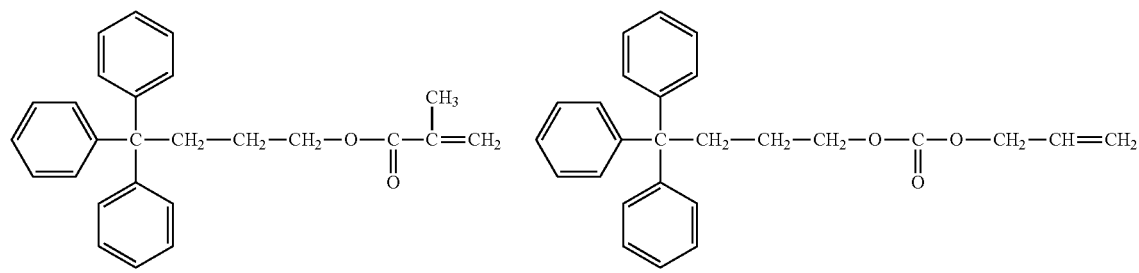

-continued
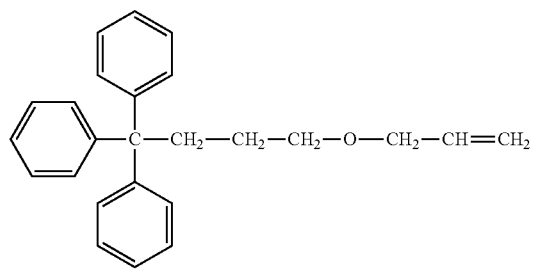
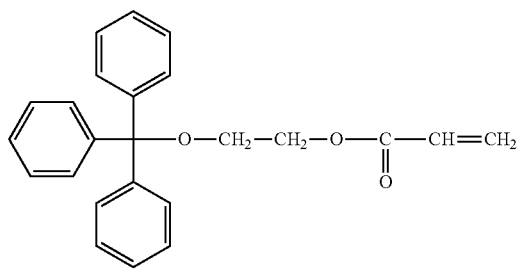
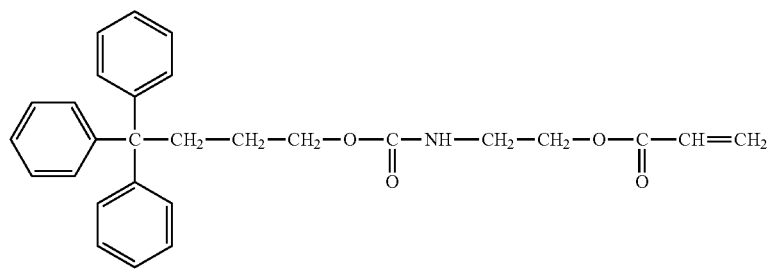
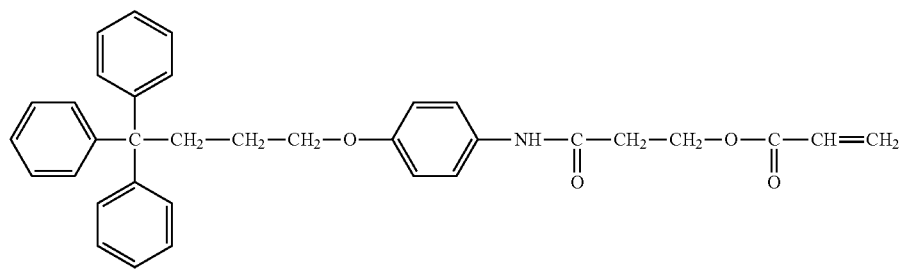
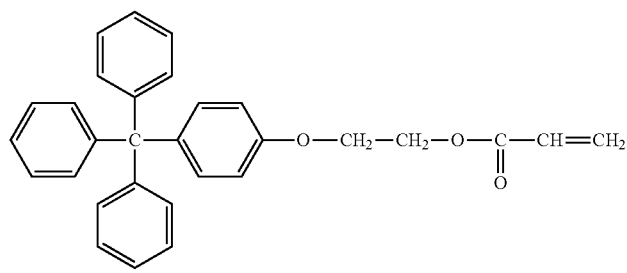
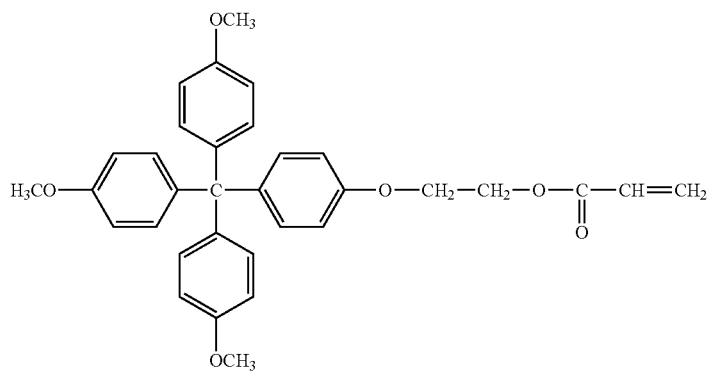

-continued

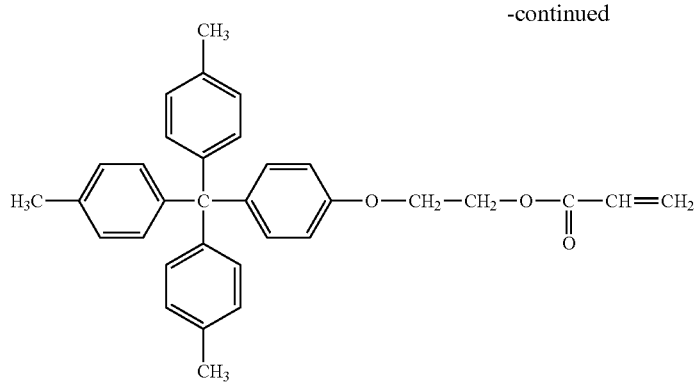

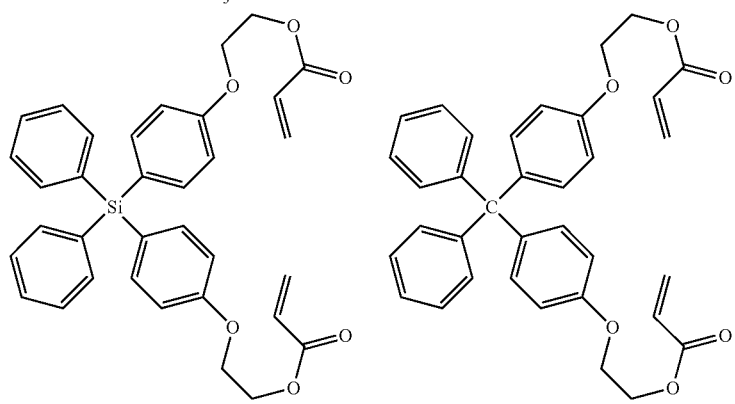

The compound represented by formula (I) according to the present invention can be produced by a known method and can be produced, for example, by the methods described in Japanese unexamined Patent Application Publication No. 63-145287 and WO2009/139476.

Specific examples are as follows.

1) In Case of 3-(Meth)acryloyloxypropyltriphenylsilane or 3-Allyloxycarbonyloxypropyltriphenylsilane 3-(Meth)acryloyloxypropyltriphenylsilane or 3-allyloxycarbonyloxypropyltriphenylsilane is produced by reacting 3-hydroxypropyltriphenylsilane, obtained by hydrolyzing an adduct of commercial triphenylsilane and allyl acetate with an alkali, with (meth)acrylic acid chloride or allyl chloroformate in the presence of a dehydrochlorinating agent such as pyridine or triethylamine.

2) In Case of 3-Allyloxypropyltriphenylsilane

3-Allyloxypropyltriphenylsilane is produced by adding commercial triphenylsilane to diallyl ether.

3) In Case of 3-Acryloyloxyethyloxytetraphenylsilane

3-Acryloyloxyethyloxytetraphenylsilane is produced according to the method shown below.

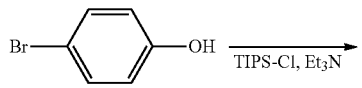

-continued

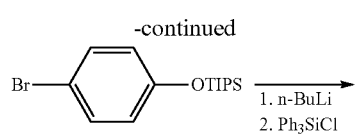

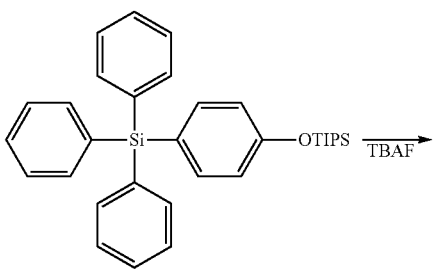

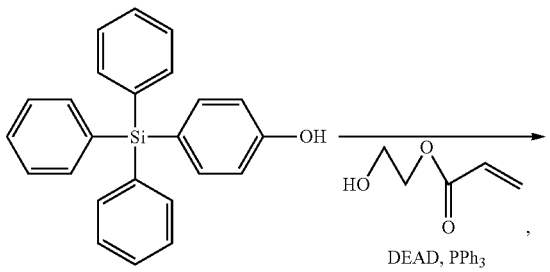

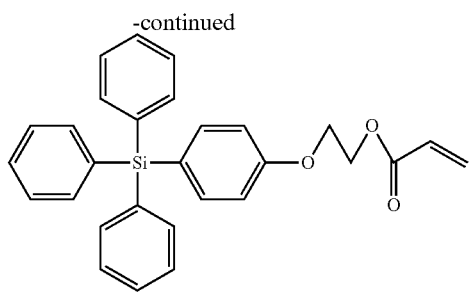

In the above formulas, TIPS represents a triisopropylsilyl group.

(Other Components)
Another Copolymerizable Compound

In addition, the coating agent of the present invention can comprise another copolymerizable compound other than the compound represented by formula (I).

The another copolymerizable compound other than the compound represented by formula (I) can be appropriately selected according to the purpose of adjusting the melting point, viscosity, refractive index, or the like and is not particularly limited. Examples of the another copolymerizable compound include the following:

a (meth)acrylate such as methyl (meth)acrylate, benzyl (meth)acrylate, phenyl (meth)acrylate, bromophenyl (meth)acrylate, ethylene glycol di(meth)acrylate, cyclohexyl (meth)acrylate, and tris(2-(meth)acryloxyethyl)isocyanate, an allyl ester such as diallyl phthalate, diallyl isophthalate, diallyl terephthalate, diethylene glycol bisallyl carbonate, triallyl cyanurate, and triallyl isocyanurate, and an aromatic olefin such as styrene, chlorostyrene, and bromostyrene.

The proportion of the compound of formula (I) included in all polymerizable compounds is preferably 30 mol % or more, more preferably 50 mol % or more.

Polymerization Initiator

In addition, the coating agent of the present invention can comprise a polymerization initiator. Here, examples of the polymerization reaction include a photopolymerization reaction and a thermal polymerization reaction. A photopolymerization reaction, which does not require the consideration of a thermal effect on a plastic substrate, is preferred. Examples of the light used in the photopolymerization reaction include ultraviolet rays or visible light. Ultraviolet rays are preferred because of the fast polymerization rate.

Examples of the photopolymerization initiator can include (a) a compound that generates a cationic species by light irradiation, and (b) a compound that generates an active radical species by light irradiation.

Examples of the compound that generates a cationic species by light irradiation include an onium salt in which the cationic moiety is a sulfonium, iodonium, diazonium, ammonium, or (2,4-cyclopentadien-1-yl)[(1-methylethyl)benzene]-Fe cation, and the anionic moiety is composed of $BF_4^-$, $PF_6^-$, $SbF_6^-$, or $[BX_4]^-$ (wherein X represents a phenyl group substituted by at least two or more fluorines or a trifluoromethyl group).

Specific examples of the sulfonium salt include bis[4-(diphenylsulfonio)phenyl]sulfide bishexafluorophosphate, bis[4-(diphenylsulfonio)phenyl]sulfide bishexafluoroantimonate, bis[4-(diphenylsulfonio)phenyl]sulfide bistetrafluoroborate, bis[4-(diphenylsulfonio)phenyl]sulfide tetrakis(pentafluorophenyl)borate, diphenyl-4-(phenylthio)phenylsulfonium hexafluorophosphate, diphenyl-4-(phenylthio)phenylsulfonium hexafluoroantimonate, diphenyl-4-(phenylthio)phenylsulfonium tetrafluoroborate, diphenyl-4-(phenylthio)phenylsulfonium tetrakis(pentafluorophenyl)borate, and triphenylsulfonium hexafluorophosphate.

Examples of the iodonium salt include diphenyliodonium hexafluorophosphate, diphenyliodonium hexafluoroantimonate, diphenyliodonium tetrafluoroborate, diphenyliodonium tetrakis(pentafluorophenyl)borate, bis(dodecylphenyl)iodonium hexafluorophosphate, bis(dodecylphenyl)iodonium hexafluoroantimonate, bis(dodecylphenyl)iodonium tetrafluoroborate, and bis(dodecylphenyl)iodonium tetrakis(pentafluorophenyl)borate.

Examples of the diazonium salt include phenyldiazonium hexafluorophosphate, phenyldiazonium hexafluoroantimonate, phenyldiazonium tetrafluoroborate, and phenyldiazonium tetrakis(pentafluorophenyl)borate.

Examples of the ammonium salt include 1-benzyl-2-cyanopyridinium hexafluorophosphate, 1-benzyl-2-cyanopyridinium hexafluoroantimonate, 1-benzyl-2-cyanopyridinium tetrafluoroborate, 1-benzyl-2-cyanopyridinium tetrakis(pentafluorophenyl)borate, 1-(naphthylmethyl)-2-cyanopyridinium hexafluorophosphate, 1-(naphthylmethyl)-2-cyanopyridinium hexafluoroantimonate, 1-(naphthylmethyl)-2-cyanopyridinium tetrafluoroborate, and 1-(naphthylmethyl)-2-cyanopyridinium tetrakis(pentafluorophenyl)borate.

Examples of the (2,4-cyclopentadien-1-yl)[(1-methylethyl)benzene]-Fe salt include (2,4-cyclopentadien-1-yl)[(1-methylethyl)benzene]-Fe(II) hexafluorophosphate, (2,4-cyclopentadien-1-yl)[(1-methylethyl)benzene]-Fe(II) hexafluoroantimonate, 2,4-cyclopentadien-1-yl)[(1-methylethyl)benzene]-Fe(II) tetrafluoroborate, and 2,4-cyclopentadien-1-yl)[(1-methylethyl)benzene]-Fe(II) tetrakis(pentafluorophenyl)borate.

Examples of the compound that generates an active radical species by light irradiation can include acetophenone, acetophenone benzyl ketal, 1-hydroxycyclohexyl phenyl ketone, 2,2-dimethoxy-1,2-diphenylethan-1-one, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, benzoin propyl ether, benzoin ethyl ether, benzyl dimethyl ketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholino-propan-1-one, 2-benzyl-2-dimethylamino-1-(4-morpholinophenyl)-butanone-1,4-(2-hydroxyethoxy)phenyl-(2-hydroxy-2-propyl)ketone, 2,4,6-trimethylbenzoyldiphenylphosphine oxide, bis-(2,6-dimethoxybenzoyl)-2,4,4-trimethylpentylphosphine oxide, and oligo(2-hydroxy-2-methyl-1-(4-(1-methylvinyl)phenyl)propanone).

The thermal polymerization initiator refers to a compound that generates a radical by heating. Examples thereof include an organic peroxide, an azo compound, and a redox initiator.

Examples of the above organic peroxide include a peroxide such as benzoyl peroxide, cumene hydroperoxide, di-t-butyl peroxide, t-butyl hydroperoxide, dicumyl peroxide, acetyl peroxide, lauroyl peroxide, cyclohexanone peroxide, dibenzoyl peroxide, and tert-butyl permaleate; a peroxycarbonate such as 1,6 bis(t-butylperoxycarbonyloxy)hexane; a peroxyketal; and a persulfate such as potassium persulfate, sodium persulfate, and ammonium persulfate.

Examples of the above azo compound can include 2,2'-azobispropane, 2,2'-dichloro-2,2'-azobispropane, 1,1'-azo(methylethyl)diacetate, 2,2'-azobisisobutane, 2,2'-azobisisobutylamide, 2,2'-azobisisobutyronitrile (AIBN), methyl 2,2'-azobis-2-methylpropionate, 2,2'-dichloro-2,2'-azobisbutane, 2,2'-azobis-2-methylbutyronitrile, dimethyl 2,2'-azobisisobutyrate, 3,5-dihydroxymethylphenylazo-2-methylmalonodinitrile, 2,2'-azobis-2-methylvaleronitrile, dimethyl 4,4'-azobis-4-cyanovalerate, and 2,2'-azobis-2,4-dimethylvaleronitrile.

Examples of the above redox initiator can include a combination such as hydrogen peroxide-iron(II) salt, organic peroxide-dimethylaniline, and cerium(IV) salt-alcohol.

For the amount of the blended polymerization initiator used in the present invention, 0.01 to 20% by mass of the polymerization initiator is preferably blended based on the total amount of all polymerizable compounds, and 0.1 to 10% by mass is further preferred.

In the present invention, a sensitizer can be added as required. For example, trimethylamine, methyldimethanolamine, triethanolamine, p-dimethylaminoacetophenone, ethyl p-dimethylaminobenzoate, isoamyl p-dimethylaminobenzoate, N,N-dimethylbenzylamine, and 4,4'-bis(diethylamino)benzophenone can be used.

(Other Components)

In addition, additive components such as a condensate of an organosilane compound, a metal compound, an organic solvent, an ultraviolet absorbing agent, a dye, a rust preventive, and a preservative can be blended into the coating agent of the present invention as required in a range that does not impair the object of the present invention.

Condensate of Organosilane Compound

The coating agent of the present invention can comprise a condensate of an organosilane compound for the purpose of laminating an organic-inorganic layer. Thus, an organic-inorganic composite film having good adhesion to a substrate can be formed.

The condensate of an organosilane compound can be produced with an organosilane compound represented by formula (II) using a known silanol condensation method.

$$R^4Si(R^3)_3 \quad (II)$$

wherein $R^4$ represents a C2 to C8 alkenyl group, a C6 to C10 aryl group, or a C1 to C30 alkyl group optionally substituted by an epoxy group, a glycidyloxy group, or a (meth)acryloxy group, and $R^3$ represents a hydroxyl group or a hydrolyzable group.

Examples of the C2 to C8 alkenyl group for $R^4$ include a vinyl group, an allyl group, and a 2-propenyl group.

Examples of the C1 to C30 alkyl group include a methyl group, an ethyl group, an n-propyl group, an isopropyl group, an n-butyl group, an isobutyl group, a s-butyl group, a t-butyl group, an n-pentyl group, an isopentyl group, a neopentyl group, a 2-methylbutyl group, a 2,2-dimethylpropyl group, an n-hexyl group, an isohexyl group, an n-heptyl group, an n-octyl group, a nonyl group, an isononyl group, a decyl group, a lauryl group, a tridecyl group, a myristyl group, a pentadecyl group, a palmityl group, a heptadecyl group, and a stearyl group.

Examples of the C6 to C10 aryl group include a phenyl group and a naphthyl group.

The hydrolyzable group of $R^3$ means, for example, a group that can be hydrolyzed by heating at 25° C. to 100° C. in the coexistence of excess water without a catalyst to produce a silanol group, or a group that can form a siloxane condensate. Specific examples thereof can include an alkoxy group, an acyloxy group, a halogen group, and an isocyanate group. An alkoxy group having 1 to 4 carbon atoms or an acyloxy group having 1 to 6 carbon atoms is preferred.

Here, examples of the alkoxy group having 1 to 4 carbon atoms include a methoxy group, an ethoxy group, a n-propoxy group, an isopropoxy group, a n-butoxy group, an isobutoxy group, and a t-butoxy group. Examples of the acyloxy group having 1 to 6 carbon atoms include an acetyloxy group and a benzoyloxy group. Examples of the halogen include a fluorine atom, a chlorine atom, a bromine atom, and an iodine atom.

In addition, the organosilane compound represented by formula (II) used in the present invention is preferably a group whose solubility parameter (SP1) obtained by Fedors' estimation method is smaller than the solubility parameter of the compound represented by formula (I) (SP2) obtained by Fedors' estimation method with a difference of 1.6 or more.

An advantage of the case where SP1 is smaller than SP2 and also the difference is 1.6 or more is that inorganic components are likely to segregate on the coating film surface.

Here, the solubility parameter (SP value) is calculated based on the following Fedors' estimation method.

Fedors' equation:

$E_v$: evaporation energy
v: molar volume
$\Delta e_i$: the evaporation energy of the atoms or atomic groups of each component
$\Delta v_i$: the molar volume of the atoms or atomic groups For the evaporation energy and molar volume of the atoms or atomic groups used in the calculation of the above equation, R. F. Fedors, Polym. Eng. Sci., 14, 147 (1974) can be referred to.

The solubility parameters (SP values) of the compound represented by formula (I) and the organosilicon compound represented by formula (II) can be calculated based on Fedors' estimation method, and therefore, the combination of the compound represented by formula (I) and the organosilicon compound represented by formula (II) can be determined based on previously calculated SP values.

For example, for the case where 3-acryloyloxypropyltriphenylsilane (SP value: 10.21) is used as the compound represented by formula (I), examples of an organosilane compound having an SP value smaller than the SP value of the triphenylsilane compound by 1.6 or more include methyltrimethoxysilane, dimethyldimethoxysilane, ethyl trimethoxysilane, vinyltrimethoxysilane, n-propyltrimethoxysilane, isopropyltrimethoxysilane, allyltrimethoxysilane, n-butyltrimethoxysilane, t-butyltrimethoxysilane, sec-butyltrimethoxysilane, isobutyltrimethoxysilane, pentyltrimethoxysilane, hexyltrimethoxysilane, cyclohexyltrimethoxysilane, and decyltrimethoxysilane (any of these has an SP value of 8.61 or less).

The mass ratio of the compound represented by formula (I) (and another copolymerizable compound when present) to the condensate of the organosilane compound represented by formula (II) in the layer is preferably 99:1 to 55:45.

The silanol condensation catalyst is not particularly limited, as long as the hydrolyzable group in the compound represented by formula (II) is hydrolyzed and the silanol is condensed to form a siloxane bond. Examples of the silanol condensation catalyst include at least one selected from the group consisting of an organic metal, an organic acid metal salt, a metal hydroxide, an acid, a base, a metal chelate compound, and a hydrolysate thereof, and a condensate thereof. Silanol condensation catalysts can be used singly, or in combinations of two or more.

Examples of the organic metal include an alkyl metal compound such as tetramethyltitanium and tetrapropylzirconium; and a metal alcoholate such as a metal propoxide, a metal isopropoxide, and a metal n-butoxide, specifically tetraisopropoxytitanium and tetrabutoxyzirconium.

The organic acid metal salt is a compound consisting of a salt obtained from a metal ion and an organic acid. Examples of the organic acid include an organic compound that exhibits acidity such as a carboxylic acid such as acetic acid, oxalic acid, tartaric acid, and benzoic acid; a sulfur-containing organic acid such as sulfonic acid and sulfinic acid; a phenol compound; an enol compound; an oxime compound; an imide compound; and an aromatic sulfonamide. Specific examples include a metal carboxylate, a metal sulfonate, and a phenol metal salt.

The metal hydroxide is a metal compound having a hydroxide ion as an anion.

The metal chelate compound is preferably a metal chelate compound having a hydroxyl group or a hydrolyzable group, more preferably a metal chelate compound having two or more hydroxyl groups or hydrolyzable groups. Having two or more hydroxyl groups or hydrolyzable groups means that the total of hydrolyzable groups and hydroxyl groups is two or more. Examples of the hydrolyzable group include an alkoxy group, an acyloxy group, a halogen group, and an isocyanate group. An alkoxy group having 1 to 4 carbon atoms and an acyloxy group having 1 to 4 carbon atoms are preferred.

In addition, as the above metal chelate compound, a β-ketocarbonyl compound, a β-ketoester compound, and an α-hydroxyester compound are preferred. Specific examples thereof include a compound in which a β-ketoester such as methyl acetoacetate, n-propyl acetoacetate, isopropyl acetoacetate, n-butyl acetoacetate, sec-butyl acetoacetate, or t-butyl acetoacetate; a β-diketone such as acetylacetone, hexane-2,4-dione, heptane-2,4-dione, heptane-3,5-dione, octane-2,4-dione, nonane-2,4-dione, or 5-methyl-hexane-2,4-dione; a hydroxycarboxylic acid such as glycolic acid or lactic acid; or the like is coordinated.

In addition, examples of the metals in these organic metal, organic acid metal salt, metal hydroxide, and metal chelate compound include titanium (Ti), zirconium (Zr), aluminum (Al), silicon (Si), germanium (Ge), indium (In), tin (Sn), tantalum (Ta), zinc (Zn), tungsten (W), and lead (Pb). Among these, titanium (Ti), zirconium (Zr), aluminum (Al), and tin (Sn) are preferred, and particularly, titanium (Ti) is preferred. These can be used singly, or in combinations of two or more.

Examples of the acid include an organic acid and a mineral acid. Specific examples of the organic acid include acetic acid, formic acid, oxalic acid, carbonic acid, phthalic acid, trifluoroacetic acid, p-toluenesulfonic acid, and methanesulfonic acid. Specific examples of the mineral acid include hydrochloric acid, nitric acid, boric acid, and hydrofluoboric acid.

Here, the acid also encompasses a photo-acid-generating agent that generates an acid by light irradiation, specifically, diphenyliodonium hexafluorophosphate, triphenylphosphonium hexafluorophosphate, and the like.

Examples of the base include a strong base such as tetramethylguanidine and tetramethylguanidylpropyltrimethoxysilane; an organic amine, a carboxylic acid-neutralized salt of an organic amine, and a quaternary ammonium salt.

The blending ratio of the silanol condensation catalyst to the mass of the organosilane compound is 1:99 to 99:1, preferably 1:99 to 50:50.

Metal Compound

A metal compound can be added to the coating agent of the present invention for the purpose of increasing the refractive index and hardness of the formed layer. Examples of the metal compound include the above-described organosilane compound, and the organic metal, the organic acid metal salt, the metal hydroxide, and the metal chelate compound illustrated as the silanol condensation catalyst. Examples of a metal compound other than these include a metal oxide. Specific examples thereof include particles of a metal oxide, silicon dioxide, titanium oxide, aluminum oxide, chromium oxide, manganese oxide, iron oxide, zirconium oxide (zirconia), or cobalt oxide. Particularly, zirconium oxide is preferred.

Examples of the shape of the particles include a spherical form, a porous powder, a scaly form, and a fibrous form. A porous powder form is more preferred.

In addition, as the metal oxide particles of the present invention, colloidal metal oxide particles can also be used. Specific examples thereof can include colloidal silica and colloidal zirconium and can include water-dispersed colloidal metal oxide particles or colloidal metal oxide particles dispersed in an organic solvent such as methanol or isopropyl alcohol.

Organic Solvent

The coating agent of the present invention can comprise an organic solvent. Typical organic solvents that can be used include an ether-based compound, an ester-based compound, an aliphatic hydrocarbon-based compound, an aromatic hydrocarbon-based compound, a ketone-based compound, and an organohalide-based compound. Especially, an ether-based compound, an ester-based compound, and an aliphatic hydrocarbon-based compound are preferred in terms of safety and the like. Specific examples of the ether-based compound include diethyl ether, dipropyl ether, dibutyl ether, and diamyl ether. Specific examples of the ester-based compound include ethyl acetate, propyl acetate, butyl acetate, amyl acetate, heptyl acetate, ethyl butyrate, and isoamyl isovalerate. Specific examples of the aliphatic hydrocarbon-based compound include normal hexane, normal heptane, and cyclohexane. Specific examples of the aromatic compound include toluene and xylene. Specific examples of the ketone-based compound include methyl ethyl ketone and methyl isobutyl ketone. Specific examples of the organohalide-based compound include trichloroethane and trichloroethylene. Further, a relatively inactive solvent such as propylene glycol monomethyl ether or propylene glycol monoethyl ether can also be used. Especially, a solvent comprising an ester-based compound such as propyl acetate, butyl acetate, isoamyl acetate, heptyl acetate, ethyl butyrate, or isoamyl isovalerate having aromaticity is preferred considering that the present invention is often used in an open system in a natural environment.

2 Compact

The compact of the present invention is directly provided with a layer obtained by coating a plastic substrate with the coating agent comprising the above compound represented by formula (I) and curing the coating agent.

(Substrate)

As the substrate on which the coating agent of the present invention can be used, a plastic substrate is preferred. Examples thereof include a cycloolefin resin, a polycarbonate resin, an acrylic resin, a polyimide resin, a polyester resin, an epoxy resin, a liquid crystal polymer resin, and a polyether sulfone. Particularly, a cycloolefin resin is preferably used.

(Formation of Coating Layer)
1) Preparation of Coating Agent

The coating agent in the present invention is usually prepared by mixing the above compound represented by formula (I), and also the above condensate of the organosilane compound, photopolymerization initiator, metal compound and the like as required, in an organic solvent.

When the coating agent in the present invention comprises the condensate of the organosilane compound, it is also referred to as an organic-inorganic composite film or a composition for forming the same.

Examples of the solvent used can include the above-described organic solvents. These solvents can be used singly, or in combinations of two or more.

In addition, for the purpose of improving the hardness of the obtained coating film, a tetrafunctional silane or colloidal silica can also be added. Examples of the tetrafunctional silane can include tetraaminosilane, tetrachlorosilane, tetraacetoxysilane, tetramethoxysilane, tetraethoxysilane, tetrabutoxysilane, tetrabenzyloxysilane, tetraphenoxysilane, tetra(meth)acryloxysilane, tetrakis[2-(meth)acryloxyethoxy]silane, tetrakis(2-vinyloxyethoxy)silane, tetraglycidyloxysilane, tetrakis(2-vinyloxybutoxy)silane, and tetrakis(3-methyl-3-oxetanemethoxy)silane. In addition, examples of the colloidal silica can include water-dispersed colloidal silica and colloidal silica dispersed in an organic solvent such as methanol or isopropyl alcohol.

In addition, in order to exhibit properties such as the coloration of the obtained coating film, film thickening, the prevention of the transmission of ultraviolet rays to the base, the provision of anticorrosiveness, and heat resistance, a filler can also be separately added and dispersed. Examples of this filler include a water-insoluble pigment such as an organic pigment and an inorganic pigment, or a particulate, fibrous, or scaly metal and alloy and oxide, hydroxide, carbide, nitride, and sulfide thereof other than a pigment. Specific examples of this filler can include particulate, fibrous, or scaly iron, copper, aluminum, nickel, silver, zinc, ferrite, carbon black, stainless steel, silicon dioxide, titanium oxide, aluminum oxide, chromium oxide, manganese oxide, iron oxide, zirconium oxide, cobalt oxide, synthetic mullite, aluminum hydroxide, iron hydroxide, silicon carbide, silicon nitride, boron nitride, clay, diatomaceous earth, slaked lime, gypsum, talc, barium carbonate, calcium carbonate, magnesium carbonate, barium sulfate, bentonite, mica, zinc green, chromium green, cobalt green, viridian, Guignet's green, cobalt chromium green, Scheele's green, green earth, manganese green, pigment green, ultramarine blue, Prussian blue, blue verditer, cobalt blue, cerulean blue, copper borate, molybdenum blue, copper sulfide, cobalt violet, Mars violet, manganese violet, pigment violet, lead suboxide, calcium plumbate, zinc yellow, lead sulfide, chromium yellow, ocher, cadmium yellow, strontium yellow, titanium yellow, litharge, pigment yellow, cuprous oxide, cadmium red, selenium red, chromium vermilion, red oxide, zinc white, antimony white, basic lead sulfate, titanium white, lithopone, lead silicate, zircon oxide, tungsten white, lead zinc flower, Bantison white, lead phthalate, manganese white, lead sulfate, graphite, bone black, diamond black, thermatomic black, vegetable black, potassium titanate whiskers, and molybdenum disulfide.

In addition, additives such as a known dehydrating agent such as methyl orthoformate, methyl orthoacetate, and tetraethoxysilane, various surfactants, and a silane coupling agent, a titanium coupling agent, a dye, a dispersing agent, a thickening agent, and a leveling agent other than the above can also be added.

The amount of the solids in the solution for forming a coating layer in the present invention is preferably 1 to 90% by mass, more preferably 5 to 60% by mass.

2) Formation of Coating Layer

The coating layer of the present invention can be produced through (A) the step of applying the above-described coating agent to a substrate and drying it, and (B) the step of irradiating the coating agent with light comprising ultraviolet rays to cure the coating agent, when a photopolymerization initiator is used. When a thermal polymerization initiator is used, heating should be performed instead of light irradiation as the above (B) step.

In the coating film in the present invention, through the above (B) step, the polymerization of the compound represented by formula (I) is performed. Further, when the coating agent comprises the condensate of the organosilane compound represented by formula (II), a configuration in which the carbon atom content in the film surface portion is lower than the carbon atom content inside the film (in the vicinity of the bonding portion to the substrate) is provided, and a concentrated layer of the condensate of the silane compound can be formed on the film surface.

As the method for applying the coating agent, a known application method can be used. Examples thereof can include a dipping method, a spraying method, a bar coating method, a roll coating method, a spin coating method, a curtain coating method, a gravure printing method, a silk screen method, and an ink jet method. In addition, the thickness of the formed film is not particularly limited and is, for example, about 0.1 to 200 µm.

The drying treatment of the layer formed by applying the coating agent is, for example, preferably performed at 40 to 200° C. for about 0.5 to 120 minutes, more preferably at 60 to 120° C. for about 1 to 60 minutes.

The irradiation with ultraviolet rays can be performed, for example, using a known apparatus such as a high pressure mercury lamp, a low pressure mercury lamp, a metal halide lamp, or an excimer lamp.

(Functional Laminated Film)

A functional laminated film can be provided on the layer formed using the coating agent of the present invention.

The layer formed using the coating agent of the present invention has very good adhesiveness to a plastic substrate, and therefore, this layer can be used as an adhesive layer or an intermediate layer. A functional film with which a plastic substrate could not be conventionally directly coated can be laminated via the film of the present invention. A plurality of layers can be laminated, and it is also possible to further coat the plurality of layers with the coating agent of the present invention and further laminate a layer or layers.

Examples of the functional laminated film include a transparent conductive film and a gas barrier film.

Examples of the transparent conductive film include a film of indium oxide doped with tin (ITO film), a film of tin oxide doped with fluorine (FTO film), a film of zinc oxide doped with antimony, and a film of zinc oxide doped with indium.

The gas barrier film is not particularly limited as long as it has gas barrier properties for oxygen, water vapor, and the like. The gas barrier film is preferably a thin film of an inorganic compound, and particularly, a thin film of a metal oxide, a metal nitride, or a metal carbide having a metal element selected from the group consisting of titanium, zirconium, aluminum, silicon, germanium, indium, tin, tantalum, zinc, tungsten, and lead, or a composite thereof is preferred.

The thickness of these functional laminated films is usually 10 to 300 nm, preferably 10 to 200 nm, and more preferably 10 to 100 nm.

For the method for forming a transparent conductive film or a gas barrier film consisting of an inorganic compound on the layer formed using the coating agent, the transparent conductive film or the gas barrier film can be formed by a known method, and the formation can be performed by a physical method such as a sputtering method, a vacuum deposition method, or an ion plating method, a chemical method such as a spraying method, a dipping method, a thermal CVD method, or a plasma CVD method, or the like.

For example, according to a sputtering method or the like, for example, a film consisting of silicon oxide can be formed by using as a target a sintered body obtained by sintering a silicon compound in the presence of oxygen gas, or the like, or a film consisting of silicon oxide can also be formed by reactively sputtering metal silicon as a target in the presence of oxygen. In addition, according to a plasma CVD method, it is possible to supply silane gas together with oxygen gas and nitrogen gas into a chamber in which a plasma is generated, to react them to form a film consisting of silicon oxynitride on a substrate. In addition, according to a thermal CVD method or the like, for example, a film consisting of silicon oxide can be formed by using an organic solvent solution containing a silicon compound, or the like as an evaporant.

In the present invention, a film is preferably formed particularly by a sputtering method, a vacuum deposition method, an ion plating method, or a plasma CVD method.

In addition, when the functional laminated film is formed, the surface of the layer formed using the coating agent can be previously plasma-treated or UV ozone-treated as required.

Examples will be shown below, but the technical scope of the present invention is not limited by these Examples.

EXAMPLES 1-1 Synthesis of Compounds-1

Synthesis Example 1

Production of 3-Methacryloxypropyltriphenylsilane (A-1)

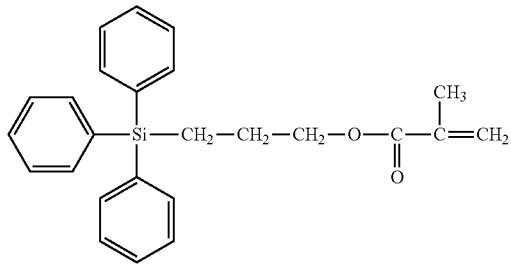 [SMILES: C=C(C)C(=O)OCCC[Si](c1ccccc1)(c1ccccc1)c1ccccc1]

The air in a reaction flask was replaced by sufficiently dry air. 25.04 g (0.0962 mol) of triphenylsilane was added to the reaction flask, and a cooling tube, a thermometer, and a nitrogen-enclosed tube were attached to the reaction flask. Then, 36.41 g (0.364 mol) of allyl acetate was added under a $N_2$ gas flow, and the mixture was stirred at room temperature under a $N_2$ gas flow. 0.5 g of an ethanol solution of chloroplatinic acid (10 wt % in terms of Pt) was dropped, and the mixture was stirred at room temperature under a $N_2$ gas flow for 3 hours. After the disappearance of the signal of Si—H (5.5 ppm) was monitored by H-NMR to confirm the completion of the reaction, excess allyl acetate was distilled off under reduced pressure, and the residue and the Pt catalyst were further column-purified to obtain 27.78 g (yield 80.1%) of 3-acetoxypropyltriphenylsilane (Mw, 360.52), a white crystal. The records of the nuclear magnetic resonance (NMR) of the obtained product are shown below. The following measurement was performed using tetramethylsilane as an internal standard and deuterated chloroform as a solvent. H-NMR spectrum: 7.4 ppm, 7.6 ppm, 4.1 ppm, 2.0 ppm, 1.8 ppm, 1.5 ppm.

12.97 g (0.036 mol) of the 3-acetoxypropyltriphenylsilane was added to a reaction flask, and a cooling tube and a thermometer were attached to the reaction flask. Then, 1 N sodium carbonate and an ethanol solution were added, and the mixture was heated at 70-80° C. for 5 hours for hydrolysis to obtain 11.4 g (0.0358 mol) of 3-hydroxypropyltriphenylsilane (Mw 318.48), a white crystal (yield 99.4%). The records of the nuclear magnetic resonance (NMR) of the obtained product are shown below. The following measurement was performed using tetramethylsilane as an internal standard and deuterated chloroform as a solvent. H-NMR spectrum: 7.4 ppm, 7.6 ppm, 3.6 ppm, 1.7 ppm, 1.4 ppm.

300 g of super-dehydrated toluene was added to a reaction flask in which the air was sufficiently replaced by a dry inert gas (nitrogen), and 5.01 g (0.01573 mol) of the 3-hydroxypropyltriphenylsilane and 1.91 g (0.01888 mol) of triethylamine were dissolved in the super-dehydrated toluene. 1.976 g (0.01890 mol) of methacrylic acid chloride was gradually added to the solution. After the completion of the dropping, the mixture was stirred at room temperature for 6 hours, and then, the reaction liquid was sequentially washed with water, 0.5 N hydrochloric acid, water, 1 N sodium carbonate, and water and dried over magnesium sulfate. The toluene was distilled off to obtain 4.976 g (0.012874 mol) of 3-methacryloxypropyltriphenylsilane (A-1) (Mw 386.56), a transparent liquid (yield 82%). The records of the nuclear magnetic resonance (NMR) of the obtained product are shown below. The following measurement was performed using tetramethylsilane as an internal standard and deuterated chloroform as a solvent. H-NMR spectrum: 7.4 ppm, 7.6 ppm, 6.4 ppm, 6.1 ppm, 5.8 ppm, 4.2 ppm, 1.8 ppm, 1.4 ppm.

Synthesis Example 2

Production of 3-Acryloxypropyltriphenylsilane (A-2)

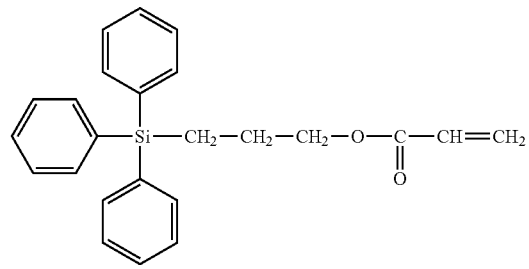 [SMILES: C=CC(=O)OCCC[Si](c1ccccc1)(c1ccccc1)c1ccccc1]

300 g of super-dehydrated toluene was added to a reaction flask in which the air was sufficiently replaced by a dry inert gas (nitrogen), and 5.28 g (0.01658 mol) of 3-hydroxypropyltriphenylsilane and 2.01 g (0.01989 mol) of triethylamine were dissolved in the super-dehydrated toluene. 1.801 g (0.0199 mol) of acrylic acid chloride was gradually added to the solution. After the completion of the dropping, the mixture was stirred at room temperature for 6 hours, and then, the reaction liquid was sequentially washed with water, 0.5 N hydrochloric acid, water, 1 N sodium carbonate, and water and dried over magnesium sulfate. The toluene was distilled off to obtain 5.56 g (0.01492 mol) of 3-acryloxypropyltriphenylsilane (A-2) (Mw 372.53), a transparent liquid (yield 89.99%). The records of the nuclear magnetic resonance (NMR) of the obtained product are shown below. The following measurement was performed using tetramethylsilane as an internal standard and deuterated chloroform as a solvent. H-NMR spectrum: 7.4 ppm, 7.6 ppm, 6.4 ppm, 6.1 ppm, 5.8 ppm, 4.2 ppm, 1.8 ppm, 1.4 ppm.

1-2 Preparation of Coating Agents-1

2 g of the above product (A-1) or (A-2) was dissolved in 8 g of methyl ethyl ketone (MEK). Then, 0.08 g of the photopolymerization initiator Irgacure (registered trademark) 907 (manufactured by BASF SE, UV polymerization initiator, 2-methyl-1-[4-(methylthio)phenyl]-2-morpholinopropan-1-one) was added, and the mixture was stirred for dissolution for 15 minutes to prepare a coating agent (B–1) or (B-2).

1-3 Preparation of Zirconia Particle-Added Coating Agent 2.5 g of (B-2) and 2.5 g of a 20 wt % MEK-dispersed zirconia colloid were mixed to obtain a coating agent (B-2').

1-4 Preparation of Organosilane Compound-Added Coating Agent

1) Synthesis of Silanol Condensation Catalyst
303.03 g of titanium diisopropoxybisacetylacetonate (manufactured by Nippon Soda Co., Ltd., T-50, the amount of solids in terms of titanium oxide: 16.5% by weight) was dissolved in 584.21 g of ethanol, and then, 112.76 g (10 times moles/the moles of titanium oxide) of ion exchange water was added with stirring. This solution was stirred for 2 hours, while being heated to 40° C., for hydrolysis. Next, the solution was filtered to obtain a yellow transparent titanium oxide nanodispersion having a concentration of 5% by weight in terms of titanium oxide [C-1]. The titanium oxide had an average particle diameter of 4.1 nm and was monodisperse.
2) Preparation of Hydrolysis Condensation Product of Organosilane Compound
As an organosilane compound, a liquid [D-1] obtained by mixing 264.76 g of vinyltrimethoxysilane (manufactured by Shin-Etsu Chemical Co., Ltd., KBM-1003) and 190.19 g of 3-methacryloxypropyltrimethoxysilane (manufactured by Shin-Etsu Chemical Co., Ltd., KBM-503) (vinyltrimethoxysilane/3-methacryloxypropyltrimethoxysilane=70/30: molar ratio) was used.
Next, a liquid [E-1] was made by mixing 453.09 g of [C-1] and 454.95 g of [D-1] at an element ratio (Ti/Si=1/9), further adding 91.96 g (2 times moles/the moles of the organosilicon compound) of ion exchange water, and stirring the mixture for 24 hours.

3) Preparation of Coating Agent (Composition for Forming Organic-Inorganic Composite Film)
The above [E-1] liquid and [B-2] liquid were mixed so that the proportion of solids was 10% by weight/90% by weight=[E-1]/[B-2], to make a coating agent (a composition for forming an organic-inorganic composite film)[B-2"].

1-5 Formation of Coating Layers-1

Film Samples
Each of the coating agents [(B-1), (B-2), (B-2'), and (B-2")] was formed into a film on a 188 μm thick COP film (ZEON Corporation, ZF-16) by a bar coater and heated at 130° C. by a warm air circulation type dryer for 3 minutes. Then, the film was irradiated with ultraviolet rays at an accumulated dose of 400 mJ/cm$^2$ by a condensing type high pressure mercury lamp (UV light comprising light having wavelengths of 365 nm, 313 nm, and 254 nm as a main component, manufactured by EYE GRAPHICS CO., LTD., 120 W/cm, lamp height of 9.8 cm, conveyor speed of 5 m/min) to obtain a thin film. Using this, film thickness measurement, a cross-cut adhesion test, and haze measurement were performed.
Refractive Index Measurement Samples
Each of the compositions for forming coating films [(B-1), (B-2), and (B-2')] was formed into a film on a silicon wafer by a dip coater and heated at 130° C. by a warm air circulation type dryer for 3 minutes. Then, the film was irradiated with ultraviolet rays at an accumulated dose of 400 mJ/cm$^2$ by a condensing type high pressure mercury lamp (UV light comprising light having wavelengths of 365 nm, 313 nm, and 254 nm as a main component, manufactured by EYE GRAPHICS CO., LTD., 120 W/cm, lamp height 9.8 cm, conveyor speed 5 m/min) to obtain a thin film.
[Measurement Conditions]
Coating Film Refractive Index
Measurement was performed using a high speed spectroscopic ellipsometer M-2000D manufactured by J.A. Woollam Co.
Film Thickness Measurement
Measurement was performed using a noncontact film thickness measuring apparatus, model F-20, manufactured by Filmetrics Japan, Inc.
Cross-Cut Adhesion Test (Adhesiveness)
According to JIS K5600, 11 vertical cuts and 11 horizontal cuts at intervals of 1 mm were made in the coating film to make a grid of 100 squares. CELLOTAPE (registered trademark) was stuck to each sample, and rubbed a plurality of times with the inner surface of a finger to adhere, and then, the tape was peeled. Evaluation was performed by the number of squares of the lattice in which the coating film was not peeled and remained.
Haze
The haze of the coating film was measured using a hazemeter (manufactured by Nippon Denshoku Industries Co., Ltd.).
Total Light Transmittance
For a film section, measurement was performed using a color and turbidity simultaneous measurement apparatus (Nippon Denshoku Industries Co., Ltd.; COH 400).

|  |  | (B-1) | (B-2) | (B-2') | (B-2") |
|---|---|---|---|---|---|
| Refractive index | 589 nm | 1.621 | 1.620 | 1.682 | — |
| Film thickness | μm | 2.5 | 2.5 | 2.5 | 2.5 |
| Adhesiveness |  | 100/100 | 100/100 | 100/100 | 100/100 |

-continued

|  |  | (B-1) | (B-2) | (B-2') | (B-2") |
|---|---|---|---|---|---|
| Haze | % | 0.4 | 0.23 | 0.36 | 0.28 |
| Total light transmittance | % | 91.48 | 92.03 | 89.89 | 90.95 |

In all substrates, no peeling of the coating layer was seen, and it was confirmed that the coating layer had excellent adhesiveness. In addition, the coating layer had excellent transparency and also a high refractive index.

2-1 Synthesis of Compounds-2

Synthesis Example 3

Diphenylmethylsilylpropyl Acrylate (A-3)

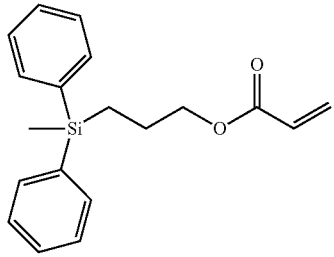 [SMILES: C=CC(=O)OCCC[Si](C)(c1ccccc1)c1ccccc1]

60.00 g of super-dehydrated THF, 7.30 g (0.02355 mol) of 3-(methyldiphenylsilyl)-1-propanol, and 4.29 g (0.0428 mol) of triethylamine were added to a reaction flask in which the air was sufficiently replaced by a dry inert gas (nitrogen), and the mixture was cooled with dissolution until the solution temperature reached 10° C. or less. 3.87 g (0.0428 mol) of acrylic acid chloride was gradually added to the solution, and the mixture was stirred for 1 hour. After the completion of the dropping, the mixture was stirred overnight at room temperature. The reaction mixture was sequentially washed with water, 0.5 N hydrochloric acid, water, 1 N sodium carbonate, and water, and the organic layer was dried over magnesium sulfate. Then, the toluene was distilled off. The residue was purified by silica gel column chromatography using an ethyl acetate/hexane mixed solvent. 6.87 g (0.02214 mol) of a compound A-3 was obtained with a yield of 94%. $^1$H-NMR spectrum: 7.6 ppm, 7.4 ppm, 6.4 ppm, 6.1 ppm, 5.7 ppm, 4.1 ppm, 1.7 ppm, 1.2 ppm, 0.5 ppm.

Synthesis Example 4

Triphenylsilylphenoxyethyl Acrylate (A-4)

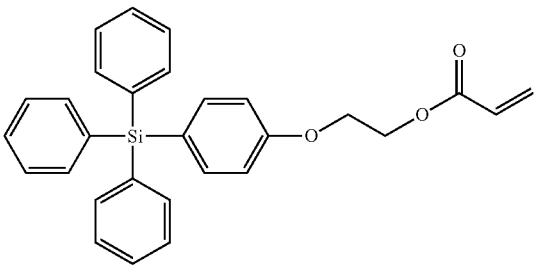 [SMILES: C=CC(=O)OCCOc1ccc([Si](c2ccccc2)(c2ccccc2)c2ccccc2)cc1]

44.00 g of THF, 3.00 g (0.00851 mol) of 4-triphenylsilylphenol, 3.35 g (0.01277 mol) of triphenylphosphine, and 1.48 g (0.01277 mol) of hydroxyethyl acrylate were added in a reaction flask and cooled with dissolution until the solution temperature reached 0° C. or less. 5.56 g (0.01277 mol) of diethyl azodicarboxylate (40% toluene solution, about 2.2 mol/L) was gradually added, and the mixture was stirred for 1 hour. Then, the mixture was stirred overnight at room temperature and then further stirred at a solution temperature of 50° C. for 3 hours. The solvent was distilled off, and then, the residue was purified by silica gel column chromatography using an ethyl acetate/hexane mixed solvent. 3.29 g (0.0076 mol) of a compound A-4 was obtained with a yield of 51%. $^1$H-NMR spectrum: 7.7 ppm, 7.4 ppm, 7.2 ppm, 6.9 ppm, 6.4 ppm, 6.2 ppm, 5.8 ppm, 4.5 ppm, 4.3 ppm.

Synthesis Example 5

Diphenylsilyldiphenoxyethyl Acrylate (A-5)

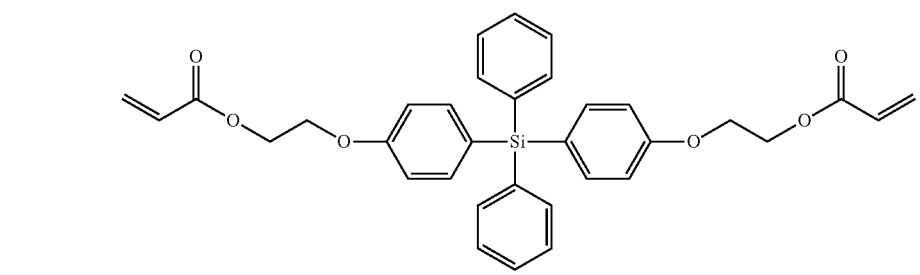 [SMILES: C=CC(=O)OCCOc1ccc([Si](c2ccccc2)(c2ccccc2)c2ccc(OCCOC(=O)C=C)cc2)cc1]

50.00 g of THF, 5.00 g (0.01357 mol) of 4,4'-diphenylsilanebisphenol, 10.68 g (0.04071 mol) of triphenylphosphine, and 4.73 g (0.04071 mol) of hydroxyethyl acrylate were added to a reaction flask and cooled with dissolution until the solution temperature reached 0° C. or less. 17.73 g (0.04071 mol) of diethyl azodicarboxylate (40% toluene solution, about 2.2 mol/L) was gradually added, and the mixture was stirred for 1 hour. Then, the mixture was stirred overnight at room temperature and then further stirred at a solution temperature of 50° C. for 3 hours. The solvent was distilled off, and then, the residue was purified by silica gel column chromatography using an ethyl acetate/hexane mixed solvent. 4.67 g (0.0083 mol) of a compound A-5 was obtained with a yield of 61%. $^1$H-NMR spectrum: 7.3-7.6 ppm, 6.9-7.0 ppm, 6.4 ppm, 6.2 ppm, 5.8 ppm, 4.5 ppm, 4.3 ppm.

Synthesis Example 6

Triphenylmethylpropyl Acrylate (A-6)

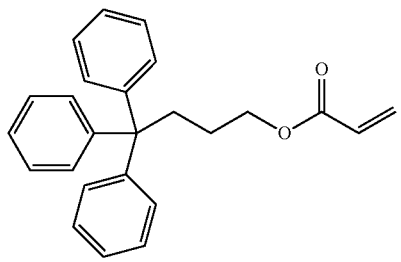 [SMILES: C=CC(=O)OCCCC(c1ccccc1)(c1ccccc1)c1ccccc1]

42.36 g of super-dehydrated THF, 5.00 g (0.01653 mol) of 4,4,4-triphenylbutanol, and 3.35 g (0.03307 mol) of triethylamine were added to a reaction flask in which the air was sufficiently replaced by a dry inert gas (nitrogen), and the mixture was cooled with dissolution until the solution temperature reached 10° C. or less. 2.24 g (0.02480 mol) of acrylic acid chloride was gradually added to the solution, and the mixture was stirred for 1 hour. After the completion of the dropping, the mixture was stirred overnight at room temperature. The reaction mixture was sequentially washed with water, 0.5 N hydrochloric acid, water, 1 N sodium carbonate, and water, and the organic layer was dried over magnesium sulfate. Then, the toluene was distilled off. The residue was purified by silica gel column chromatography using an ethyl acetate/hexane mixed solvent. 5.36 g (0.0150 mol) of a compound A-6 was obtained with a yield of 91%. $^1$H-NMR spectrum: 7.3 ppm, 7.2 ppm, 6.4 ppm, 6.1 ppm, 5.8 ppm, 4.1 ppm, 2.7 ppm, 1.5 ppm.

Synthesis Example 7

Triphenylmethylphenoxyethyl Acrylate (A-7)

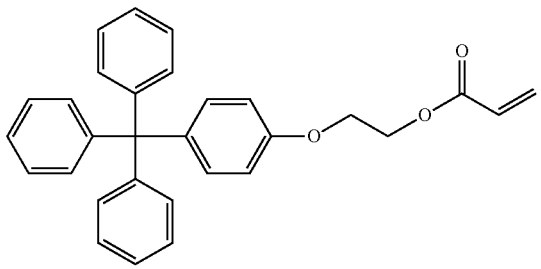

50.00 g of THF, 5.00 g (0.01486 mol) of 4-triphenylmethylphenol, 5.85 g (0.02229 mol) of triphenylphosphine, and 2.59 g (0.02229 mol) of hydroxyethyl acrylate were added to a reaction flask and cooled with dissolution until the solution temperature reached 0° C. or less. 9.71 g (0.02229 mol) of diethyl azodicarboxylate (40% toluene solution, about 2.2 mol/L) was gradually added, and the mixture was stirred for 1 hour. Then, the mixture was stirred overnight at room temperature and then further stirred at a solution temperature of 50° C. for 3 hours. The solvent was distilled off, and then, the residue was purified by silica gel column chromatography using an ethyl acetate/hexane mixed solvent. 3.29 g (0.0076 mol) of a compound A-7 was obtained with a yield of 51%. $^1$H-NMR spectrum: 7.3-7.0 ppm, 6.9 ppm, 6.4 ppm, 6.2 ppm, 5.8 ppm, 4.5 ppm, 4.3 ppm.

Synthesis Example 8

4-[Tris(4-methoxyphenyl)methyl]phenoxyethyl Acrylate (A-8)

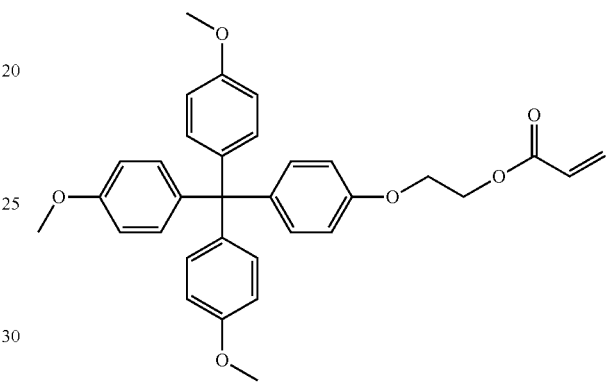

30.00 g of THF, 3.00 g (0.00703 mol) of 4-[tris(4-methoxyphenyl)methyl]phenol, 2.27 g (0.01055 mol) of triphenylphosphine, and 1.23 g (0.01055 mol) of hydroxyethyl acrylate were added to a reaction flask and cooled with dissolution until the solution temperature reached 0° C. or less. 4.56 g (0.01055 mol) of diethyl azodicarboxylate (40% toluene solution, about 2.2 mol/L) was gradually added, and the mixture was stirred for 1 hour. Then, the mixture was stirred overnight at room temperature and then further stirred at a solution temperature of 50° C. for 3 hours. The solvent was distilled off, and then, the residue was purified by silica gel column chromatography using an ethyl acetate/hexane mixed solvent. 2.03 g (0.00387 mol) of a compound A-8 was obtained with a yield of 55%. $^1$H-NMR spectrum: 7.1 ppm, 7.0 ppm, 6.9 ppm, 6.7 ppm, 6.4 ppm, 6.2 ppm, 5.8 ppm, 4.5 ppm, 4.3 ppm.

Synthesis Example 9

Diphenylmethyldiphenoxyethyl Acrylate (A-9)

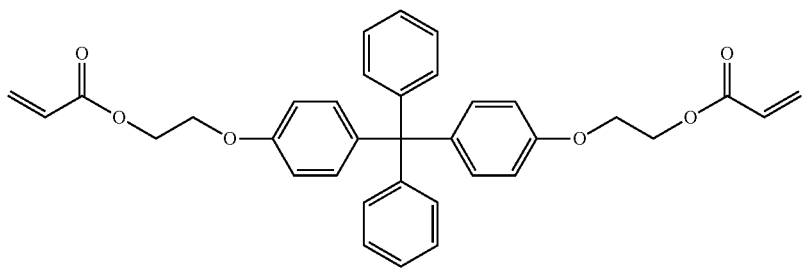 [SMILES: C=CC(=O)OCCOc1ccc(C(c2ccccc2)(c2ccccc2)c2ccc(OCCOC(=O)C=C)cc2)cc1]

50.00 g of THF, 5.00 g (0.01419 mol) of 4,4'-dihydroxytetraphenylmethane, 11.16 g (0.04256 mol) of triphenylphosphine, and 4.94 g (0.04256 mol) of hydroxyethyl acrylate were added to a reaction flask and cooled with dissolution until the solution temperature reached 0° C. or less. 18.53 g (0.04256 mol) of diethyl azodicarboxylate (40% toluene solution, about 2.2 mol/L) was gradually added, and the mixture was stirred for 1 hour. Then, the mixture was stirred overnight at room temperature and then further stirred at a solution temperature of 50° C. for 3 hours. The solvent was distilled off, and then, the residue was purified by silica gel column chromatography using an ethyl acetate/hexane mixed solvent. 3.66 g (0.0067 mol) of a compound A-9 was obtained with a yield of 51%. $^1$H-NMR spectrum: 7.3-7.0 ppm, 6.9 ppm, 6.4 ppm, 6.2 ppm, 5.8 ppm, 4.5 ppm, 4.3 ppm.

Synthesis Example 10

Triphenylsilylpropoxycarbonylaminoethyl Acrylate (A-10)

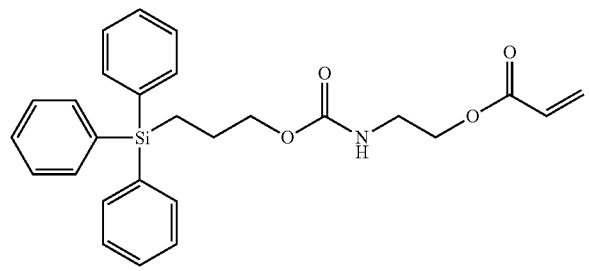 [SMILES: C=CC(=O)OCCNC(=O)OCCC[Si](c1ccccc1)(c1ccccc1)c1ccccc1]

50.00 g of toluene, 2.50 g (0.01884 mol) of 2-isocyanatoethyl acrylate, 5.04 g (0.01570 mol) of 3-triphenylsilyl-1-propanol, and a catalytic amount of dibutyltin laurate were added to a reaction flask subjected to nitrogen replacement, and the mixture was heated with dissolution until the solution temperature reached 70° C. The solution was reacted for 6 hours. After the completion of the reaction, the reaction solution was cooled to room temperature, and 20 g of distilled water was placed to deactivate the unreacted isocyanate compound. The solvent of the organic layer was distilled off, and then, the residue was purified by silica gel column chromatography using an ethyl acetate/hexane mixed solvent. 5.84 g (0.01272 mol) of a compound A-10 was obtained with a yield of 81%. $^1$H-NMR spectrum: 7.2-7.5 ppm, 6.4 ppm, 6.1 ppm, 5.8 ppm, 4.9 ppm, 4.2-4.1 ppm, 3.5 ppm, 1.8 ppm, 1.4 ppm.

2-2 Preparation of Coating Agents-2

1 g of each of the above compounds (A-3) to (A-9) was added to 4 g of cyclohexane, and the mixture was stirred until the compound was completely dissolved. Then, 0.04 g of the photopolymerization initiator Irgacure (registered trademark) 907 (manufactured by BASF SE, UV polymerization initiator, 2-methyl-1-[4-(methylthio)phenyl]-2-morpholino-propan-1-one) was added to make each of coating agents (B-3) to (B-9).

2-3 Formation of Coating Layers-2

Each of the coating agents of (B-3) to (B-9) was formed into a film on the following plastic base by bar coating and heated at 100° C. by a warm air circulation type dryer for 3 minutes. The film was irradiated with ultraviolet rays at an accumulated dose of 400 mJ/cm$^2$ by a condensing type high pressure mercury lamp (UV light comprising light having wavelengths of 365 nm, 313 nm, and 254 nm as a main component, manufactured by EYE GRAPHICS CO, LTD., one lamp type, 120 W/cm, lamp height 9.8 cm, conveyor speed 5 m/min) to obtain a thin film.

Substrate 1: PET film, COSMOSHINE A4300 (188 μm), Toyobo Co., Ltd.

Substrate 2: PEN film, Teonex Q65F (125 μm), Teijin DuPont

Substrate 3: acrylic plate, DELAGLAS A (2 mm), Asahi Kasei Corporation

Substrate 4: polyimide, Kapton 500H (126.7 μm), DU PONT-TORAY CO., LTD.

Adhesiveness Test

An adhesiveness test was performed according to the cross-cut method of JIS K5600-5-6.

In all substrates, no peeling of the coating layer was seen, and it was confirmed that the coating layer had excellent adhesiveness.

2-4 Formation of Coating Layers-3

Each of the coating agents of (B-4) to (B-8) was formed into a film on the following plastic base by bar coating and heated at 100° C. by a warm air circulation type dryer for 3 minutes. The film was irradiated with ultraviolet rays at an accumulated dose of 400 mJ/cm$^2$ by a condensing type high pressure mercury lamp (UV light comprising light having wavelengths of 365 nm, 313 nm, and 254 nm as a main component, manufactured by EYE GRAPHICS CO., LTD., one lamp type, 120 W/cm, lamp height 9.8 cm, conveyor speed 5 m/min) to obtain a thin film.

Substrate 5: COP plate, ZEONOR 1600 (1 mm), ZEON Corporation

Substrate 6: COP plate, ZEONOR 1430R (1 mm), ZEON Corporation

Substrate 7: COC plate, TOPAS COC 5018L-10 (1 mm), Polyplastics Co., Ltd.

Substrate 8: COC plate, TOPAS COC 6017S-04 (1 mm), Polyplastics Co., Ltd.

Adhesiveness Test

An adhesiveness test was performed according to the cross-cut method of JIS K5600-5-6.

In all substrates, no peeling of the coating layer was seen, and it was confirmed that the coating layer had excellent adhesiveness.

2-5 Formation of Coating Layers-4

Each of the coating agents of (B-4) and (B-6) to (B-8) was formed into a film on the following plastic base by bar coating and heated at 100° C. by a warm air circulation type dryer for 3 minutes. The film was irradiated with ultraviolet rays at an accumulated dose of 400 mJ/cm$^2$ by a condensing type high pressure mercury lamp (UV light comprising light having wavelengths of 365 nm, 313 nm, and 254 nm as a main component, manufactured by EYE GRAPHICS CO., LTD., one lamp type, 120 W/cm, lamp height 9.8 cm, conveyor speed 5 m/min) to obtain a thin film.

Substrate 9: COP film, ZEONOR Film ZF-14 (188 μm), ZEON Corporation (stretched film)

Substrate 10: COP film, ZEONOR Film ZF-16 (188 μm), ZEON Corporation (stretched film)

Substrate 11: PET film, Lumirror T60, Toray Industries, Inc. (stretched film)

Adhesiveness Test

An adhesiveness test was performed according to the cross-cut method of JIS K5600-5-6.

In all substrates, no peeling of the coating layer was seen, and it was confirmed that the coating layer had excellent adhesiveness.

2-6 Formation of Functional Laminated Films

Using each of the coating agents (B-2), (B-2'), (B-2"), (B-4), (B-6), and (B-7), a coating layer was made by the method described in 1-5 in Examples. About 40 nm of a film of indium oxide doped with tin (ITO film) was laminated on this thin film by a DC sputtering method.

Adhesiveness Test

An adhesiveness test was performed according to the cross-cut method of JIS K5600-5-6. No peeling of the ITO film was seen, and it was confirmed that the coating layer had excellent adhesiveness.

The invention claimed is:
1. A coating solution comprising:
a compound represented by formula (I):

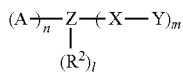

wherein
A represents

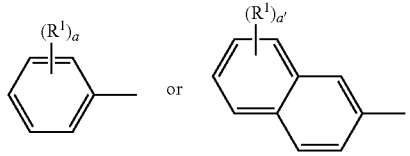

wherein $R^1$ represents an electron-donating group, a represents an integer of 0 to 5, and a' represents an integer of 0 to 7, Z represents a carbon atom or a silicon atom, $R^2$ represents a hydrogen atom, a hydroxyl group, a linear or branched C1 to C6 alkyl group, a linear or branched C1 to C6 alkoxy group, a C3 to C6 cyclic alkyl group, or a C3 to C6 cyclic alkoxy group, X represents, when Z is a carbon atom,
  (i) a C1 to C20 alkylene group optionally comprising an oxygen atom, a sulfur atom, a selenium atom, a C3 to C6 divalent aliphatic ring group, a C6 to C10 arylene group, an amide structure, a urethane structure, or —NR— wherein R represents a hydrogen atom or a C1 to C6 alkyl group;
  (ii) one of the following groups:

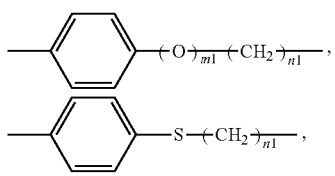

wherein m1 represents an integer of 0 or 1, n1 represents an integer of 1 to 20, n2 represents an integer of 1 to 10, n3 and n4 each independently represent an integer of 1 to 10, and R represents a hydrogen atom or a C1 to C6 alkyl group;
  (iii) a C3 to C10 divalent aliphatic ring group; or
  (iv) a C6 to C10 arylene group;
and when Z is a silicon atom,
  a C1 to C20 alkylene group comprising a sulfur atom, a selenium atom, an amide structure, a urethane structure, or —NR— wherein R represents a hydrogen atom or a C1 to C6 alkyl group;

Y represents —O—CO—(O)$_{m2}$—CR=CH$_2$ with m2 representing 0 or 1 and R representing a hydrogen atom or a methyl group; —CH=CH$_2$; an allyloxy group; an allyloxycarbonyloxy group; an epoxy group;

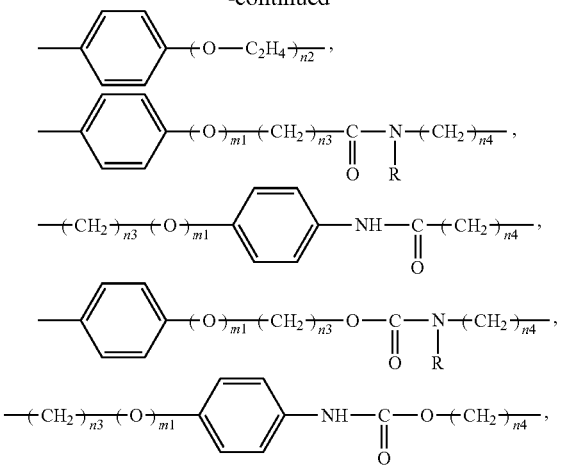

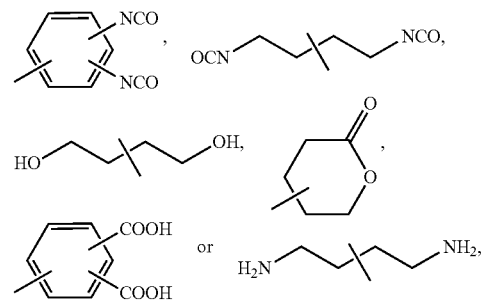

n represents an integer of 2 or 3,
m represents an integer of 1 or 2,
l represents an integer of 0 or 1, and n+m+l=4; and
when n represents an integer of 2 or 3, A is the same or different; and
an organic solvent,
wherein:
a total amount of all solids in the coating solution is in the range of 1 to 90% by mass, and
the compound represented by formula (I) constitutes 30 mol % or more of all polymerizable compounds in the coating solution.

2. The coating solution according to claim 1, further comprising a condensate of an organosilane compound represented by formula (II):

$$R^4Si(R^3)_3 \qquad (II)$$

wherein R⁴ represents a C2 to C8 alkenyl group, a C6 to C10 aryl group, or a C1 to C30 alkyl group optionally substituted by an epoxy group, a glycidyloxy group, or a (meth) acryloxy group, and R³ represents a hydroxyl group or a hydrolyzable group.

3. The coating solution according to claim 1, wherein the total amount of all solids in the coating solution is in the range of 5 to 60% by mass.

4. The coating solution according to claim 1, wherein the compound represented by formula (I) constitutes 50 mol % or more of all polymerizable compounds in the coating solution.

5. The coating solution according to claim 1, wherein the total amount of all solids in the coating solution is in the range of 1 to 20.63% by mass.

6. The coating solution according to claim 1, wherein m represents 1.

7. The coating solution according to claim 6, wherein Z is a carbon atom.

8. The coating solution according to claim 6, further comprising a metal compound.

9. The coating solution according to claim 1, wherein:
n represents 3,
m represents 1, and
l represents 0; and
A is the same or different.

10. The coating solution according to claim 9, wherein Z is a carbon atom.

11. The coating solution according to claim 9, further comprising a metal compound.

12. The coating solution according to claim 1, further comprising a metal compound.

13. The coating solution according to claim 12, wherein the metal compound is zirconia.

14. The coating solution according to claim 12, wherein the metal compound is a metal oxide.

15. The coating solution according to claim 1, wherein Z is a carbon atom.

16. The coating solution according to claim 12, wherein in the formula (I), X is

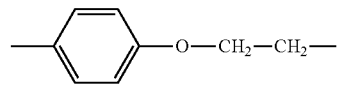

and Y is —O—CO—CH=CH₂, and the compound represented by the formula (I) is a compound represented by the following formula:

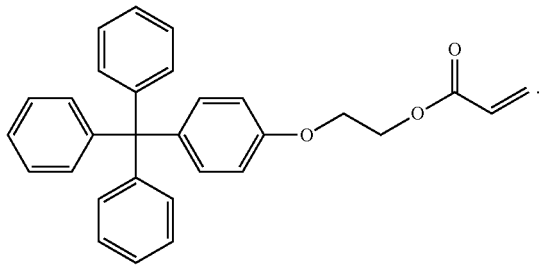 [SMILES: C=CC(=O)OCCOc1ccc(C(c2ccccc2)(c2ccccc2)c2ccccc2)cc1]

17. The coating solution according to claim 15, further comprising a condensate of an organosilane compound represented by formula (II):

$$R^4Si(R^3)_3 \quad\quad (II)$$

wherein R⁴ represents a C2 to C8 alkenyl group, a C6 to C10 aryl group, or a C1 to C30 alkyl group optionally substituted by an epoxy group, a glycidyloxy group, or a (meth) acryloxy group, and R³ represents a hydroxyl group or a hydrolyzable group.

18. The coating solution according to claim 15, further comprising a metal compound.

19. The coating solution according to claim 18, wherein the metal compound is zirconia.

20. A method comprising:
applying the coating solution according to claim 1 to a substrate.

* * * * *